United States Patent
Greenberg

(10) Patent No.: US 10,042,161 B2
(45) Date of Patent: Aug. 7, 2018

(54) EYE PROJECTION SYSTEM

(71) Applicant: EYEWAY VISION LTD., Or Yehuda (IL)

(72) Inventor: Boris Greenberg, Tel Aviv (IL)

(73) Assignee: EYEWAY VISION LTD., Tel Aviv (IL)

( * ) Notice: Subject to any disclaimer, the term of this patent is extended or adjusted under 35 U.S.C. 154(b) by 0 days.

(21) Appl. No.: 15/122,603

(22) PCT Filed: Mar. 3, 2014

(86) PCT No.: PCT/IL2014/050210
§ 371 (c)(1),
(2) Date: Aug. 30, 2016

(87) PCT Pub. No.: WO2015/132775
PCT Pub. Date: Sep. 11, 2015

(65) Prior Publication Data
US 2017/0068091 A1    Mar. 9, 2017

(51) Int. Cl.
*G02B 27/00* (2006.01)
*G06F 3/01* (2006.01)
(Continued)

(52) U.S. Cl.
CPC ....... *G02B 27/0093* (2013.01); *G02B 26/101* (2013.01); *G02B 27/017* (2013.01);
(Continued)

(58) Field of Classification Search
CPC ............. G02B 26/101; G02B 27/0093; G02B 27/017; G02B 27/0172; G02B 27/104;
(Continued)

(56) References Cited

U.S. PATENT DOCUMENTS 5,596,339 A    1/1997    Furness, III et al.
6,943,754 B2   9/2005    Aughey et al.
(Continued)

FOREIGN PATENT DOCUMENTS

CN    101583898    11/2009
CN    102906623     1/2013
(Continued)

OTHER PUBLICATIONS

International Search Report from International Application No. PCT/IL2014/050210 dated Jul. 1, 2014.

*Primary Examiner* — Stephen G Sherman
(74) *Attorney, Agent, or Firm* — Dorsey & Whitney LLP

(57) ABSTRACT

An eye projection system is disclosed, including an image generator and an eye projection optical module. The image generator is adapted to obtain data indicative of an image, produce a plurality of light beam portions corresponding to pixels of the image, adjust the intensity of each light beam portion in accordance with a value of a pixel of the image corresponding thereto and direct the light beam portion to propagate along a general optical propagation path towards the eye projection optical module with a projection angle $\alpha_{scn}$, relative to the general optical propagation path, which is determined in accordance with a location of the respective pixel in the image. The eye projection optical module includes a gaze tracking deflector responsive to input signals indicative of a gaze direction β of a user eye and configured and operable to deflect the general optical propagation path of the light beam portions towards the location of the pupil of the user eye associated with the gaze direction β. The general optical propagation path is deflected such that the light beam portions incident on the pupil with pupil incidence angles $\alpha_{in}$ with respect to a line of sight of the pupil, where the pupil incidence angles $\alpha_{in}$ correspond to the projection angles $\alpha_{scn}$. The system thereby provides direct
(Continued)

projection of the image onto the retina of the eye at a specific location on the retina regardless of the gaze direction β of the eye.

22 Claims, 6 Drawing Sheets

(51) Int. Cl.
    *G02B 26/10*     (2006.01)
    *G02B 27/10*     (2006.01)
    *G02B 27/01*     (2006.01)
    *G02C 11/00*     (2006.01)
    *A61B 3/113*     (2006.01)
    *G02B 5/20*     (2006.01)

(52) U.S. Cl.
    CPC ........ G02B 27/0172 (2013.01); G02B 27/104 (2013.01); G02C 11/10 (2013.01); G06F 3/013 (2013.01); *A61B 3/113* (2013.01); *G02B 5/20* (2013.01); *G02B 2027/0138* (2013.01); *G02B 2027/0178* (2013.01)

(58) Field of Classification Search
    CPC .............. G02B 5/20; G02B 2027/0138; G02B 2027/0178; G02C 11/10; G06F 3/013; A61B 3/113
    See application file for complete search history.

(56) References Cited

U.S. PATENT DOCUMENTS

| | | |
|---|---|---|
| 7,542,210 B2 | 6/2009 | Chirieleison, Sr. |
| 7,637,615 B2 | 12/2009 | Yamada |
| 7,936,519 B2 | 5/2011 | Mukawa et al. |
| 8,289,231 B2 | 10/2012 | Budd et al. |
| 8,384,999 B1 | 2/2013 | Crosby et al. |
| 2004/0109135 A1 | 6/2004 | Watanabe et al. |
| 2007/0159599 A1 | 7/2007 | Yamada |
| 2008/0151185 A1 | 6/2008 | Saito et al. |
| 2010/0045571 A1 | 2/2010 | Yamamoto |
| 2011/0213664 A1 | 9/2011 | Osterhout et al. |
| 2012/0154277 A1 | 6/2012 | Bar-Zeev et al. |
| 2013/0021226 A1* | 1/2013 | Bell .................... G02B 3/0006 345/8 |
| 2013/0044042 A1 | 2/2013 | Olsson et al. |

FOREIGN PATENT DOCUMENTS

| | | |
|---|---|---|
| JP | 10319342 | 12/1998 |
| JP | 2005505787 | 2/2005 |
| JP | 2006058505 | 3/2006 |
| JP | 2008145701 | 6/2008 |
| JP | 2010091944 | 4/2010 |
| JP | 2010139575 | 6/2010 |
| JP | 2010175829 | 8/2010 |
| JP | 2013210587 | 10/2013 |
| WO | WO0079327 | 12/2000 |
| WO | WO02101444 | 12/2002 |
| WO | WO2006019028 | 2/2006 |
| WO | 2006/078177 | 7/2006 |
| WO | 2009/094643 | 7/2009 |
| WO | 2010/054473 | 5/2010 |
| WO | 2011/106798 | 9/2011 |
| WO | 2012/082807 | 6/2012 |
| WO | 2013/117999 | 8/2013 |
| WO | 2013/163468 | 10/2013 |
| WO | 2014/030158 | 2/2014 |
| WO | WO2014031326 | 2/2014 |

* cited by examiner

200

- 210 – Obtaining data indicative of the gaze direction β

- 220 – Obtaining the scan angle $α_{scn}$ of the image scanner 118

- 230 – Determining the intensity/chromatic content of the projected pixel
  - 232 – Associating the scan angle $α_{scn}$ with corresponding pixel $P_i$ in the image (e.g. using an image scan mapping S')
  - 234 – Obtaining pixel data including intensity and possibly also the chromatic content of the pixel $P_i$

- 240 – Operating the image generator 116 to adjust the intensity/chromatic content of the input light beam ILB, or of a respective portion thereof, in accordance with the pixel data
  - 242A – Operating the intensity modulator IM of the image generator's SLM in accordance with the pixel data
  - 242B – Operating the respective cell of the SLM image generator's SLM 116 in accordance with the pixel data

- 250 – Adjusting the deflection angle of the gaze tracking deflector in accordance with the gaze direction β to direct the light beam to be incident on the pupil with a pupil incidence angle $α_{in}$ corresponding to the pixel Pi

Fig.3

EYE PROJECTION SYSTEM

TECHNOLOGICAL FIELD

The present invention is in the field of image projections systems and is particularly related to wearable/head mounted image projection systems adapted for projecting images to a user eye(s) for providing pure or augmented virtual reality experience to users.

BACKGROUND

Head mounted or otherwise wearable image projection system for projecting virtual and/or augmented virtual reality to the user eye(s) are becoming increasingly popular. Such systems are in many cases configured as glasses mountable onto a use's head and operable for projecting images to the user's eyes for providing virtual reality image/video projection to the user. To this end, certain of the known systems are aimed at providing pure virtual reality image projections to the user eyes, in which light from the external scenery is blocked from reaching the eye(s), while other systems are directed to provide augmented virtual reality perception, in which the light from the external scenery is allowed to pass to the eyes, while also being augmented/superposed by images/video frames projected to the eyes by the image projection systems.

For example, U.S. patent application No. 2013044042 discloses an electronic device including a frame configured to be worn on the head of a user. The frame can include a bridge configured to be supported on the nose of the user and a brow portion coupled to and extending away from the bridge and configured to be positioned over a side of a brow of the user. The frame can further include an arm coupled to the brow portion and extending to a free end. The first arm can be positionable over a temple of the user with the free end disposed near an ear of the user. The device can also include a transparent display affixed to the frame adjacent the brow portion and an input affixed to the frame and configured for receiving from the user an input associated with a function. Information related to the function can be presentable on the display.

U.S. Pat. No. 7,936,519 disclosed a head mounted display including: an eyeglasses frame-like frame to be mounted onto an observer's head; and two image display devices, each of the image display devices including an image generating device, and light guide means which is mounted to the image generating device, which as a whole is located on the side of the center of an observer's face relative to the image generating device, on which beams emitted from the image generating device are incident, through which the beams are guided, and from which the beams are emitted toward an observer's pupil.

U.S. Pat. No. 8,289,231 discloses a head mounted virtual image display unit which is compact in size and weight, and incorporates a high performance optical system offering a clear see-through capability. A sliding light shield may be incorporated for those instances when see-through capability is not desired. A focus adjustment may be incorporated to permit the focusing of the image, for example, at a distance of approximately 18 inches to infinity. An adjustable headband may be incorporated that adapts to fit the users head. A flexible boom structure may be incorporated to facilitate fine positional adjustment of the optical assembly. A slider and ball joint mechanism may also be incorporated to facilitate positional adjustment of the optical assembly. A built-in microphone may be incorporated to enable speech input by the user. The head mounted virtual image display unit may be used comfortably in conjunction with eye or safety glasses, and provides a useful image to the user without blocking his view of the surrounding environment. The unit is designed to have a pleasing appearance so as to greatly enhance user acceptability.

U.S. Pat. No. 8,384,999 disclosing an optical module for head mounted displays and other applications. The optical module includes an optical substrate and optical superstrate having inter-engaging ridged surfaces. A reflective layer is formed on at least one of the surfaces. An index matching material may be located between the surfaces. A region that receives a projected image, from a projector, directs rays launched from the projector onto the ridged surfaces, so that in use a viewer perceives an augmented image. The augmented image includes reflected rays from the projector and transmitted rays from an object located on an opposite side of the module to that of the viewer.

In certain techniques eye position and movement are tracked to determine a focal region for the user. A technique tracking gaze is disclosed for example in U.S. Pat. No. 6,943,754.

U.S. patent application No. 2012154277 discloses a method and system that enhances a user's experience when using a near eye display device, such as a see-through display device or a head mounted display device is provided. An optimized image for display relative to a field of view of a user in a scene is created. The user's head and eye position and movement are tracked to determine a focal region for the user. A portion of the optimized image is coupled to the user's focal region in the current position of the eyes, a next position of the head and eyes predicted, and a portion of the optimized image coupled to the user's focal region in the next position.

U.S. Pat. No. 7,542,210 discloses a head mounted display device having a mount which attaches the device to a user's head, a beam-splitter attached to the mount with movement devices, an image projector which projects images onto the beam-splitter, an eye-tracker which tracks a user's eye's gaze, and one or more processors. The device uses the eye tracker and movement devices, along with an optional head-tracker, to move the beam-splitter about the center of the eye's rotation, keeping the beam-splitter in the eye's direct line-of-sight. The user simultaneously views the image and the environment behind the image. A second beam-splitter, eye-tracker, and projector can be used on the user's other eye to create a stereoptic, virtual environment. The display can correspond to the resolving power of the human eye. The invention presets a high-resolution image wherever the user looks.

International patent application publication No. WO 2013/117999 discloses systems, methods and computer program products for gaze tracking. An exemplary method includes directing light into an eye using a projector; detecting, using an image-capturing module, a reflection from a surface associated with the eye; and determining a line of sight associated with the eye based on the detected reflection. In some embodiments, the light comprises infra-red light. In some embodiments, the projector comprises a laser. In some embodiments, the projector comprises a liquid crystal on silicon (LCOS) chip. In some embodiments, the surface associated with the reflection is at least one of the cornea, the iris, or the retina.

GENERAL DESCRIPTION

Conventional projection systems for providing virtual or augmented reality to users are generally based on the projection of an image (e.g. a video image) towards the user eyes such that the image is perceived by the user eye as being located/focused at an intermediate image plane located a certain distance in front of the eye (e.g. typically a distance of about 4 to several meters away from the eye.). The intermediate image plane, onto which the image is projected, may be a real image plane in front of the eye (i.e. at which the projected light beams forming the image are actually focused) or a virtual image plane (i.e. at which the projected light beams forming the image are perceived to be focused by the user eye). In any case, in such conventional image projection systems, the intermediate image plane has to be optically relayed to the user's eye. In other words, as the intermediate image plane (be it virtual or real image plane) is typically placed at a certain finite distance in front of the eye, it is thus focused onto the eye retina only when the eye lens focuses to that certain distance.

One major deficiency of conventional virtual/augmented reality imaging techniques, which project images perceived at a certain finite distance from the user eyes, relates to the development of eye fatigue, and in many cases, headaches. This problem is even more particularly immanent, when stereoscopic images are independently projected to each of the user eyes to create a perceived 3D illusion. This is because, within the thus generated 3D illusion, there may be objects/elements which are perceived by the user to be located at various different distances from the eyes, which causes the eyes to attempt to continuously refocus the eye lenses to such different distances. However, as indicated above, the actual image, which each eye perceives, is actually located/focused at a real or virtual image plane that is at a certain, typically fixed, distance from the eye. Accordingly, the "eyes" attempt to focus to different distances in accordance with the perceived distances of the elements/object within the image, generally fail, thus confusing the visual sensory mechanisms in the brain, yielding eye fatigue and headaches.

Another major deficiency of conventional techniques relates to eye movements. In conventional techniques, where the image perceived by each of the eyes is projected on an image plane in front of the eyes, the image plane is typically associated with a reference frame that is either fixed with respect to a reference frame of the external scenery/environment where the user is located (as is the case in typical 3D movie theaters where a real image is projected onto a fixed screen in the theater), or it is fixed with respect to a reference frame associated with the user's head (as is the case with pilot's or gamers' helmets, which are designed to project augmented/virtual reality to their users). In any of these cases, the projected image is not fixed to the reference frame of the eye (i.e. line of sight of the eyeball), which results with the known problem of target-sight alignment to the projection module, and requires specific calibrations. Accordingly it is difficult to utilize conventional techniques for projecting an image on arbitrary chosen locations on the retina, while the user eyes move. Such traits are however particularly desired in certain applications for augmenting visual user perception with additional information, such as from the Internet.

In this connection, in binocular human vision, the eyes (lines of sight) are not always directed to parallel optical axes, but are in many cases directed such that their optical axes intersect (e.g. at a location associated with an object at which the person is looking). Accordingly, it is often desired to individually adjust the projection of images to the retina of each eye individually and independently so as to compensate or take into account the binocular disparity between the eyes. This is also difficult to achieve with conventional techniques in which the images are projected onto image planes which are not fixed to the reference frame of each of the eyes, but are fixed either to a reference frame of the external scenery, or to a reference frame of the user's head.

The present invention provides a novel eye projection technique, which is usable for solving the above deficiencies of the known in the art techniques. More particularly, the present invention provides systems and methods for direct projection of images onto an eye retina, and additionally provides systems and methods for directing the projection/imaging optical path so as to track the location of the eye in accordance with its gaze direction. This enables for projecting images onto specific/fixed locations on the eye retina, while the gaze direction changes.

It should be understood that the phrase fixed location on the retina is used herein to refer to a specific location on the retina which corresponds to a specific visual angle. In this regards, it should be noted that small saccadic movements (tremor) of the image on the retina (which are effected by saccadic movements of the eye) are needed in order that the image on the retina will appear stable and fixed in the specific visual angle/direction. To this end, the phrase fixed/specific location location on the retina should be understood as a location on the retina which is fixed to the extent to the extent permitted by the saccadic eye movement, but which may not be absolutely fixed in some cases and may slightly move due to the saccadic eye movements. Accordingly, it should be noted that the technique of the present invention, which is described in more details below, provides for compensating for large movement of the eye (e.g. associated with changes in the gaze direction), while small eye movement, such as saccadic movements (tremor), may not be compensated, while still permitting the image to appear completely stable on the fixed location.

According to some aspects of the present invention, there is provided a system and a method for direct imaging on an eye retina. The projection system includes an image scanner including a first adjustable optical deflector (e.g. one or more fast scanning mirrors operable to perform two dimensional image scanning such as a raster scan). The image scanner is configured and operable to receive an input light beam and deflect it so as to adjust an angle of incidence of the light beam with the pupil of the user eye. To this end, the first adjustable optical deflector of the image scanner performs image scanning, such as a raster scan, during which the light beam is deflected such that it is incident on the pupil with various pupil incident angles $\alpha_{in}$ corresponding to various locations on a retina of the eye. In turn, the intensity, and possibly also the spectral content of the light beam, is modulated in accordance with the image to be projected on the retina, such that respective pixels of the image are projected onto the various locations of the retina during the image scanning. In other words, the pupil incident angles $\alpha_{in}$ correspond to the pixels in the image and cause these pixels to directly project onto respective locations on the retina.

The system of the present invention also includes an eye projection optical module located in an optical path of the light beam propagating towards the eye. Typically, according to some embodiments of the present invention, the eye projection optical module includes an angular beam relay module, which is configured and operable for receiving the light beam from the image scanner propagating therefrom with a certain output image projection angle $\alpha_{scn}$, with respect to the optical axis, and relaying the light beam to be incident on the pupil with the corresponding pupil incident angle $\alpha_{in}$. To this end, $\alpha_{in}$ may be a monotonic function $F_{opt}$ of the output image projection angle $\alpha_{scn}$: $\alpha_{in} \equiv \{\alpha^x_{in}, \alpha^y_{in}\} = F_{opt}(\alpha_{scn}) \equiv F_{opt}(\{\alpha^x_{scn}, \alpha^y_{scn}\})$, where the superscript indices X and Y designate the angles measured with respect to two orthogonal lateral axes perpendicular to the optical path. In this connection, the monotonic function $F_{opt}$, which maps the projection angle $\alpha_{scn}$ of the image scanner to the pupil incidence angle $\alpha_{in}$, is generally associated with the optical operation/function of the eye projection optical module which relays the light beam from the image scanner to the pupil. The image projection angle $\alpha_{scn}$ may in turn correspond to the two dimensional location $\{P_x, P_y\}$ of the corresponding pixel in the image $\alpha_{scn} = \{\alpha^x_{scn}, \alpha^y_{scn}\} = S(\{P_x, P_y\})$. Here, S is the image scan function (also referred to herein as image scan mapping function) which maps between a location $\{P_x, P_y\}$ of pixel in the image and a angular state/position $\alpha_{scn}$ of the image scanner.

As indicated above, one of the prominent deficiencies of conventional techniques is that the projected image captured by the eye is not fixed to the eye coordinates (reference frame), but to another reference frame, be it the reference frame of the scenery external to the eye, or the reference frame of the user's head. Accordingly, when the gaze direction of the eye changes, the location of the projection of the image on the eye retina changes accordingly. This is because the actual pupil incidence angle $\alpha_{in}$ depends on the gaze direction. For example, marking the gaze direction by $\beta \equiv \{\beta^x, \beta^y\}$, for a given projection angle $\alpha_{scn}$ the pupil incidence angle $\alpha_{in}$ will be as follows:

$$\alpha_{in} = F_{opt}(\alpha_{scn}) - \beta = F_{opt}(S(\{P_x, P_y\})) - \beta. \quad \text{Eq. (1)}$$

This will result in dependence between the projected location of the pixels on the retina (which depends on pupil incidence angle $\alpha_{in}$) and gaze direction $\beta$.

Therefore, according to the present invention, the function $F_{opt}(S(\{P_x, P_y\}))$ should be modified in order to compensate for changes in the gaze direction $\beta$ of the pupil, to allow projection of the image pixels on specific (e.g. fixed) locations on the retina in various/changing gaze directions.

This can be achieved by utilizing a specifically configured eye projection optical module associated with a modified optical function, $F'_{opt}$ which is tunable in accordance with the gaze direction. For example, replacing the optical function $F_{opt}$ in Eq. (1) above by the modified optical function $F'_{opt}$ as follows:

$$F'_{opt}(\alpha_{scn}, \beta) = F_{opt}(\alpha_{scn}) + \beta, \quad \text{Eq. (2)}$$

will result in the pupil incidence angle $\alpha_{in}$ being invariant to the gaze direction. Indeed, according to some embodiments of the present invention this solution is implemented by including, in the eye projection optical module, a tunable gaze tracking deflector, being a second adjustable optical deflector (e.g. including an addressable mirror). The gaze tracking deflector is configured and operable to be responsive to signals indicative of a gaze direction $\beta$ of the eye for deflecting the optical propagation path of the light beam in accordance with the gaze direction $\beta$ such that said light beam is incident on the pupil with said angle $\alpha_{in}$ with respect to the gaze direction (with respect to the optical axis of the pupil, i.e. line of sight thereof).

Alternatively or additionally, invariance of the pupil incidence angle $\alpha_{in}$ to the gaze direction may be achieved by utilizing suitable mapping between image pixels and the image scan mirrors. Such mapping takes into account and compensates for changes in the gaze direction $\beta$ (e.g. tunable in accordance with the gaze direction). For example, utilizing a modified image scan mapping function S' that satisfies the following:

$$F_{opt}(S'(\{P_x, P_y\}, \beta)) = F_{opt}(S(\{P_x, P_y\})) + \beta. \quad \text{Eq. (3)}$$

To this end, another way to provide at least a partial remedy to changes in the gaze direction $\beta$ is by modifying the image scan function S to at least partially compensate, for $\beta$ to enable preserving the pixel projections on the same locations on the retina. In other words, image scan function S is modified by changing the correspondence between the projection angle $\alpha_{scn}$ and the image pixels (light intensity) projected at this angle of the image scanner, in accordance with $\beta$. This can thus be achieved by implementing suitable digital processing to determine a selected portion of the image to be projected on the retina. Upon change in the gaze direction changes, the selected portion of the image is shifted to compensate for the shift in gaze direction.

This approach may however require using an image projection system having an extended field of view and capable of projecting pixel related light beams at extreme incident angles to cover the entire range of possible pupil orientations at different gazes. However, designing and manufacturing of an optical image projection system supporting such extreme incident angles on the eye, might be associated with deteriorated optical performance and/or with high tolerance constraints making the production of such system either non-feasible or non-cost effective for certain applications.

Also it should be noted that, when the gaze direction $\beta$ changes, also does the spatial location of the pupil. Therefore using the modified image scan function S' of equation (3) to compensate for $\beta$ may require use of a sufficiently wide light beam, with width covering some or all of the possible pupil locations. For example, the gaze direction $\beta$ of the eye may be at any angle within a solid angle $\Omega \approx 60°$. Accordingly, as typical eyeball diameter D is about 25 mm, the pupil can be located at an area of nominal radius of 6 mm. Therefore, utilizing the gaze direction $\beta$ may require that the light beam directed to the eye will be of equivalent radius (e.g. of about 8 mm) so that it indeed reaches the pupil at various gaze directions.

As further discussed below, in some cases it is desirable to direct to the pupil light beams whose widths/radius are smaller than the pupil's widths/radius. This may be used to improve the depth of focus of the image projection on the retina. However, it should be noted that using the scheme of Equation (3) for compensating for the gaze direction by using the image scan function S', may not be desired in such embodiments where narrow light beams (e.g. narrower than the pupil) are used. This is because it would require the beams to be much wider than the pupil and to cover a substantial portion of the possible pupil locations.

However, use of wide light beams, wider than the pupils, may not be required in embodiments in which the eye projection optical module is specifically configured for compensating for the gaze direction $\beta$ (namely in embodiments in which the eye projection optical system is tunable/adjustable according to the gaze direction—as in Eq. (2)). This is because, in such embodiments, the eye projection optical module may include gaze tracking deflector operating in accordance the gaze direction $\beta$, to deflect the optical propagation path of the light beam towards the pupil. This allows using the light beam(s) narrower than the pupil's width while still tracking and directing these light beam(s) towards the pupil at various gaze directions thereof. For example, in some embodiments, the gaze tracking deflector may include an addressable mirror deflecting the light beam to different deflection angles in accordance with the gaze direction $\beta$ so as to change the optical path of the light beam deflected therefrom. The gaze tracking deflector may also include a field selector optical module (e.g. including one or more lenses or mirrors) configured and operable to receive beams of light propagating from the addressable mirror along various respective optical paths corresponding to different gaze directions, and direct them towards corresponding spatial locations at which the pupil is located when at these different gaze directions respectively. The field selector optical module may, for example, include a-spherical optics, such as an off-axis parabolic deflector which is specifically configured for carrying out this function. In some embodiments the field selector optical module of the eye tracking deflector module includes, or is formed by one or more optical surfaces of an eyeglass lens.

Indeed, in a more general way, a combination of the techniques indicated above with references to Eq. (2) and (3) may also be used, by utilizing both the eye projection optical module and the pixel mapping processing, to compensate for the gaze direction β (e.g. such that each of the functions provides partial and complementary compensation). This might require that the following condition is satisfied by the mapping function S' and the optical function F':

$$F'_{opt}(S'(\{P_x,P_y\},\beta-\beta_1),\beta_1)=F_{opt}(\alpha_{scn})+\beta. \quad \text{Eq. (4)}$$

where $\beta_1$ is the part of the gaze direction angle β which is compensated by the tunable gaze tracking deflector of the eye projection optical module, and $(\beta-\beta_1)$ is the part of the gaze direction angle β, which is compensated by processing (by tuning the mapping function S').

Thus, the invention provides systems and methods for direct projection of images on the eye retina. This may be achieved according to the invention without a need for projecting/focusing the image on either a real or a virtual intermediate image plane located external to the eye at a fixed distance therefrom. Accordingly, discomfort, fatigue or headaches, associated with the perception of the images at such intermediate image planes, are generally relieved, and possibly entirely eliminated. As will be described more specifically below, direct projection of images on the eye retina is achieved using an image projection system, adapted to output light beams, corresponding to different image pixels, at different respective output image projection angles associated with the locations of the respective pixels in the image, and utilizing an angular relay optics to relay the light beams outputted from the image projection system onto the eye pupil with corresponding pupil incidence angles. The angular relay optics provides that the angle of a light beam incident on the pupil, corresponds to the output angle at which the light beam emanated from the image projection system, and in turn it also corresponds to the respective pixel of the image. Because the eye lens focuses on light beams, which impinge thereon from different directions, onto different respective regions of the retina, the system therefore provides for direct imaging of the image onto the retina.

In some embodiments, the system of the present invention is adapted to direct collimated light beams to the pupil. Accordingly, such light beams are perceived by the eye as arriving from an "infinite" distance and the eye lens needs not to be focused at any image plane located at a finite distance therefrom. This provides for relieving discomforting phenomena associated with such focusing, as discussed above.

Alternatively, or additionally, the direct projection technique of the invention provides for projecting images onto the eye retina, in a manner that the images are projected with enhanced depth of focus on the retina. Accordingly, the image is projected substantially focused on the retina, at substantially any focal state of the eye lens. For example, the image may be projected with substantial depth of focus allowing it to remain focused on the retina, while the eye lens is at any focal state within a wide focal length range from 4 meter to ∞. According to the invention, projection of images with increased depth of focus is achieved by projecting onto the eye pupil light beams associated with the image pixels, where the widths of the beam is narrower than the diameter of eye pupil. To this end, in typical optics the depth of focus is associated with the pupil diameter of the optical system Smaller pupil diameters provide wider depth of focus and vice versa. This is the same for the optical system of the eye. However, according to the present invention, the images are directly projected onto the eye retina by directing light beams corresponding to the image pixels directly towards the eye pupil (without forming an intermediate image plane). Accordingly, the inventors have found that by utilizing and directing light beams with narrow beam widths, narrower than the pupil's diameter, the focal depth of the image projected on the retina is increased. In fact, the focal depth of the image on the retina is increased because the effective diameter of the pupil, through which the light beams enter the eye to interact with the eye-lens, equals in such a case, to the diameter of the light beams (which are less than the actual diameter of the pupil). This is used in some embodiments of the present invention for relieving and possibly entirely eliminating discomfort, fatigue or headaches, associated with the attempts of the eye to focus on the projected image, since at any reasonable focal state of the eye lens, the image remains focused. Accordingly, in some embodiments of the present invention, an optical system capable of projecting onto the eye light beams narrower than the pupil's diameter, is used.

Also in some embodiments, laser light (e.g. coherent light) is used as a light source, and optionally also a suitable beam collimator is utilized to provide sufficiently narrow and optionally collimated light towards the pupil.

In some embodiments light beams with width being in the order of 60% of a typical pupil radius (e.g. which is about 1.5 mm) are used to provide the sufficiently large depth of field/focus of the image on the retina. In this connection, according to the invention due to the large depth of field obtained when using/projecting of such narrow light beams, e.g. narrower than the pupil, on to the eye, a need for adjustable focusing and associated optics may be obviated. Accordingly, in some embodiments of the present invention, a system with fixed/non-adjustable focus may be used for directing the light beams to the eyes.

Thus, according to one broad aspect of the present invention there is provided an eye projection system including an image generator and an eye projection optical module. The image generator is configured to obtain data indicative of an image, produce a plurality of light beam portions corresponding to pixels of the image, adjust the intensity of each light beam portion in accordance with a value of a respective pixel of the image corresponding thereto and direct the light beam portion to propagate along a general optical propagation path towards the eye projection optical module. The light beam portion is directed to propagate to the eye projection optical module with a projection angle $\alpha_{scn}$ relative to the general optical propagation path, where the projection angle $\alpha_{scn}$ is determined in accordance with the location of the respective pixel in the image. The eye projection optical module includes a gaze tracking deflector configured and operable to be responsive to input signals indicative of a gaze direction β of a user eye, for deflecting the general optical propagation path of the light beam portions towards the pupil of the eye in accordance with the gaze direction $\beta$. The general optical propagation path is deflected such that the light beam portions incident on the pupil with pupil incidence angles $\alpha_{in}$, corresponding to the projection angles $\alpha_{scn}$, with respect to a line of sight of the pupil at that gaze direction $\beta$. The system thereby provides for directly projecting the image onto the retina of the eye at a substantially fixed location on the retina regardless of the gaze direction $\beta$ of the eye.

According to some embodiments of the present invention the correspondence between the projection angle $\alpha_{scn}$ and the pupil incidence angle $\alpha_{in}$ is such that the pupil incidence angle $\alpha_{in}$ is a monotonic function of the projection angle $\alpha_{scn}$.

According to some embodiments of the present invention the eye projection system includes one or more beam collimators adapted for effecting a collimation of the light beam portions such that the light beam portions incident on the pupil while being substantially collimated thereby enabling direct projection of the image on the eye retina. For example the direct projection of the image on the retina may be characterized by the image being perceived by the eye as originating from an infinite distance from the eye.

According to some embodiments of the present invention the eye projection system includes one or more optical modules adapted for effecting widths of the light beam portions, such that the widths are smaller than a diameter of the pupil. This thereby enables projection of said image on the retina with an extended depth of focus. According to some embodiments of the present invention the gaze tracking deflector of the eye projection system includes an addressable optical deflecting unit and a field selector optical module. The addressable optical deflecting unit is located along the general optical propagation path, and the field selector optical module is located along the optical path downstream from the addressable optical deflecting unit with respect to a light propagation direction through the system. In some embodiments the addressable optical deflecting unit is responsive to the input signals indicative of the gaze direction $\beta$ and is operable for adjusting its deflection angle to deflect a light beam incident thereon to propagate along a respective optical path corresponding to the gaze direction $\beta$. The field selector optical module may be configured and operable to receive beams of light propagating along various respective optical paths corresponding to different gaze directions $\beta$ and direct them towards corresponding locations of the pupil which are associated with the different gaze directions $\beta$ respectively. To this end in certain embodiments of the present invention the field selector optical module includes an a-spherical optics, such as an off-axis parabolic deflector.

According to some embodiments of the present invention the eye projection optical module of the eye projection system further includes an angular beam relay module. The angular beam relay module is configured and operable for receiving each of the light beam portions propagating from the image generator at various projection angles $\beta_{scn}$, and relaying the light beam portions to be projected onto the pupil (at its location) with corresponding pupil incidence angles $\alpha_{in}$ respectively. For example, in some embodiments the angular beam relay module includes first and second optical modules that are respectively associated with first and second focal lengths. The first and second optical modules are spaced apart from one another along the general optical propagation path by an optical distance that is substantially equal to a sum of the first and second focal lengths.

In certain embodiments of the present invention the addressable optical deflecting unit of the gaze tracking deflector is located along in the optical path between the first and second optical modules of the angular beam relay module. Also in some embodiments the second optical module of the angular beam relay and the field selector optical module are integral in a common optical element.

According to some embodiments of the present invention the image generator of the eye projection system includes:
  a light module providing an input light beam;
  an image scanner located in the optical path of the input light beam and adapted to split the input light beam into one or more light beam portions and directing the one or more of light beam portions to propagate with the projection angles $\alpha_{scn}$ relative to the general optical propagation path;
  a light intensity modulator located in an optical path of at least one of the input light beam and the one or more light beam portions and adapted for controllably adjusting the intensity of one or more of light beam portions; and
  a projection controller connectable to the light intensity modulator module and configured and operable to obtain image data indicative of image pixels to be projected onto the eye retina and operate the light intensity modulator module for adjusting the intensities of the light beam portion in accordance with a value of a pixel of the image corresponding to the light beam portions respectively.

In certain embodiments the projection controller is also connectable to the image scanner and is operable to direct said light beam portion to propagate with the projection angles $\alpha_{scn}$ relative to the general optical propagation path.

For example, in some embodiments the light intensity modulator may include a spatial light modulator configured and operable for splitting the input light beam into the plurality of light beam portions propagating along distinct respective optical paths, and the image scanner may include a static optical module configured for deflecting the plurality of light beam portions towards different projection angles $\alpha_{scn}$.

Alternatively or additionally, the light intensity modulator may be adapted to modulate the intensity of the input light beam, and the image scanner may include a scanning mirror adapted for splitting the input light beam in to the plurality of light beam portions (temporal portions), and directing them to propagate towards different angles $\alpha_{scn}$.

To this end, according to some embodiments of the present invention the eye projection system includes at least two adjustable optical deflectors (e.g. two adjustable two-dimensional optical deflectors, each being formed by one or more rotatable mirrors). For example, a first adjustable optical deflector may include or may be associated with, the at least one scanning optical deflector of the image scanner, and a second adjustable optical deflector may include, or may be associated with, the gaze tracking deflector of the gaze tracking deflector.

In some embodiments, the at least two (e.g. first and second) adjustable optical deflectors are actuated to control two or more degrees of freedom of the propagation of the light beam portions to direct the light beam portions to be incident on the pupil location at different gaze directions $\beta$, and with a desired pupil incidence angle $\alpha_{in}$ with respect to a line of sight of the eye in the different gaze directions $\beta$.

The pupil incidence angles $\alpha_{in}$ are also adjusted by the at least two adjustable optical deflectors to correspond to the respective pixels of the image associated with the light beam portions respectively.

For example the second adjustable optical deflector is configured and operable for controlling intersection locations of the light beam portions propagating towards the pupil with a substantially spherical portion of a virtual surface defining the possible locations of the pupil when the user eye gazes in different directions. The first adjustable optical deflector is configured and operable for controlling an angle of intersection of the light beam portions with a substantially spherical portion of the virtual surface defining the possible locations of the pupil. Alternatively, the optical functions of the first and second optical deflectors may be mixed and a certain mapping (e.g. lookup table) may be used to associate the respective positions (e.g. the respective orientations) of the two deflectors) with the intersection location and the intersection angle of the light beam portions on the virtual surface defining the possible locations of the pupil.

According to some embodiments of the present invention, the eye projection system includes one or more beam collimators that are adapted for controlling a degree of collimation of the light beam portion incident on the pupil (e.g. configured such that the light beam portions are substantially collimated when incident on the pupil). Alternatively or additionally the one or more beam collimator may be configured such that a width of the light beam portions is substantially narrower than the pupil diameter when the light beam portions are incident on the pupil.

According to another broad aspect of the present invention there are provided and eye glasses including one or more eye projection systems (e.g. two eye projection systems) similar to the above described eye projection systems. The eye glasses may be configured for projecting pure and/or augmented virtual reality to the eye. In the later case a lens of the eye glasses may include a beam splitter/combiner surface adapted for reflecting light from the eye projection system towards the user eye and transmitting external light from a scenery towards the user's eye. For example, the input light beam of the eye projection system may include one or more spectral bands, and the beam splitter/combiner surface may be configured as a notch filter adapted for reflecting said one or more spectral bands towards the user's eye. Alternatively or additionally, the input light beam may include light polarized to a certain polarization, and the beam splitter/combiner surface may be configured as a polarizer adapted for reflecting that certain polarization towards the user eye.

According to yet another broad aspect of the present invention there is provided an eye projection system for projecting images on a retina of a user's eye. The eye projection system includes a light module for producing an input light beam of controllable intensity and an optical system arranged in an optical path of the input light beam. The optical system include a first and second adjustable two-dimensional optical deflectors and a controller adapted to receive data indicative of an image to be projected onto a retina of the user's eye, and data indicative of a gaze direction β of said eye, and for projecting pixels of the image onto corresponding locations on the retina. Projecting the images on the retina may include carrying out the following for projection of each pixel of the image:

operating the light module to produce the input light beam having intensity corresponding to an intensity value of the pixel in the image;

operating at least one of the first and second two-dimensional optical deflectors by adjusting its deflection angle to direct the input light beam in accordance with said gaze direction β to be incident on a pupil of the user's eye; and operating at least one of the first and second two-dimensional optical deflectors by adjusting its deflection angle to direct the light beam to be incident on the pupil with a pupil incidence angle $\alpha_{in}$ corresponding to a location of the pixel in the image to thereby enable focusing, by an eye lens, a portion of the light beam associated with the pixel onto a location on the retina corresponding to the location of the pixel in the image.

BRIEF DESCRIPTION OF THE DRAWINGS

In order to better understand the subject matter that is disclosed herein and to exemplify how it may be carried out in practice, embodiments will now be described, by way of non-limiting example only, with reference to the accompanying drawings, in which:

FIG. 3 is a flowchart 200 showing a method according to an embodiment of the present invention for projecting images on an eye retina;

Figure 1:
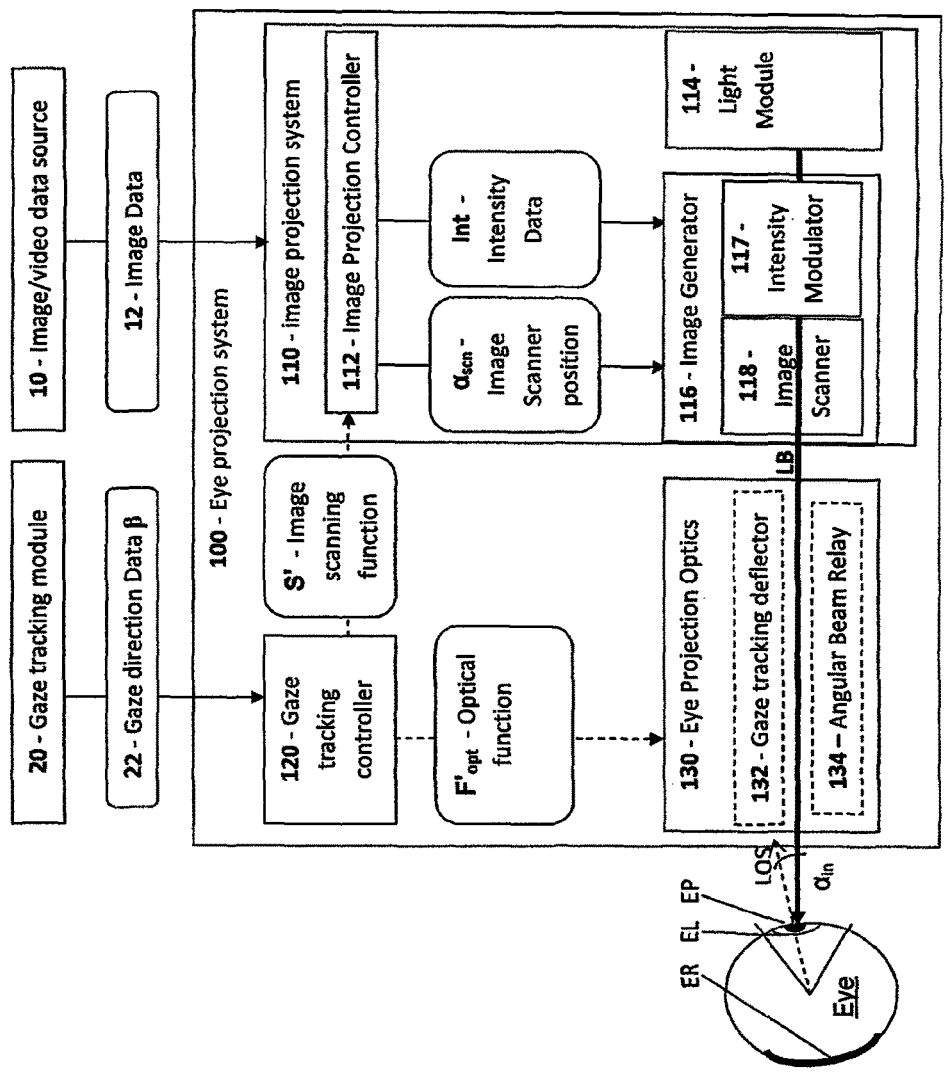
FIG. 1 is a functional block diagram 100 of an eye projection system configured and operable according to some embodiments of the present invention.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF EMBODIMENTS

In the following detailed description, numerous specific details are set forth in order to provide a thorough understanding of the presently disclosed subject matter. However, it will be understood by those skilled in the art that the presently disclosed subject matter may be practiced without some of these specific details. In other instances, well-known methods, procedures and components have not been described in detail so as not to obscure the presently disclosed subject matter.

It is appreciated that, unless specifically stated otherwise, certain features of the presently disclosed subject matter, which are, for clarity, described in the context of separate embodiments, may also be provided in combination in a single embodiment. Conversely, various features of the presently disclosed subject matter, which are, for brevity, described in the context of a single embodiment, may also be provided separately or in any suitable sub-combination.

It should also be understood that the optical modules/elements described below and in particularly those illustrated in FIGS. 2A to 2D, 4 and 5, designate functional optical elements/modules and configurations thereof which are used for implementing the invention. Accordingly, the optical elements/modules are described below in accordance with their functional operations. It should be noted that these optical elements/modules can be implemented practically by utilizing various arrangements combinations of actual optical elements. Additionally in certain embodiments of the present invention, two or more of the functional optical modules described below may be implemented integrally in a common optical module/element, and/or a single functional optical element/module described below may be actually implemented utilizing several separate optical elements. To this end, a person of ordinary skill in the art, knowing the present invention, will readily appreciate the various configurations of optical elements/modules and the various arrangements of such modules, for implementing the present invention and the optical functions of the functional optical element/modules described below.

Reference is made to FIG. 1 showing a functional block diagram 100 of an eye projection system configured and operable according to some embodiments of the present invention. The eye projection system 100 includes an image projection system 110, an eye projection optics 130.

The image projection system 110 is adapted to obtain data indicative of an image to be projected on the eye, produce a plurality of light beam portions LB corresponding to pixels of the image. The image projection system 110 is also adapted to adjust the intensity of each light beam portion $LB_i$, of the light beam portions LB with a value of a pixel of the image corresponding to the respective portion and direct the light beam portion to propagate to eye projection optical module 130 with a certain projection angle $\alpha_{scn}$ associated with a location of the respective pixel in the image. In turn eye projection optical module is configured and operable to be responsive to input signals indicative of a gaze direction β of a user eye for deflecting the optical propagation path of the light beam portions LB towards a pupil of the user eye in accordance with the gaze direction β. The general optical propagation path is deflected such that the light beam portions LB incident on the pupil with pupil incidence angles $\alpha_{in}$ corresponding to the projection angles $\alpha_{scn}$ (e.g. irrespectively if the gaze direction β). In this connection it should be understood that the term pupil incidence angles are used herein to indicate an angle of incidence of light beam, or a portion thereof, on the pupil, as measured with respect to the light of sight of the pupil/eye.

To this end, the invention provides for partially or entirely compensating for different gaze direction of the eye by directing to pixel' associated light beam portions LB to incident with predetermined incidence angles on the eye pupil corresponding to the image location of the pixels associated with these light beam portions.

In this connection it should be noted that the light beam portions LB may be spatial portions/segments of an input light beam ILB which may be segmented/splitted spatially or temporally by an image scanner module 118 of the image projection system 110. As will be described in more details below, the scanner module 118 may be implemented utilizing a spatial light modulator and/or a scanning mirror (e.g. a raster mirror scanner) operable for splitting the light beam to spatial or temporal light beam portions propagating along the general optical path towards the eye projection optical module 130.

It should be noted that for clarity, in the following, the light beam portions LB, which are produced by the image scanner 118 are referred to interchangeably as light beams or as light beam portions.

According to some embodiments of the present invention the eye projection system 100 may also include and a gaze tracking controller 120 connectable to at least one of the image projection system 110 and the eye projection optics 130 and adapted for adjusting the operations of at least one of them in accordance with a gaze direction β of the eye/pupil (namely in accordance with the pupil's line of sight LOS). The image projection system 110 is configured and operable for projection of images by scanning a light beam over a range of projection angles $\alpha_{scn}$ corresponding to locations of pixels in the image data 12 to be projected, while controlling the intensity Int and possibly chromatic (spectral) Spc content of the light beam in accordance with the respective intensity and chromatic content values of the projected pixels of the image.

To this end, the image projection system 110 typically includes a light source/module 114 producing an input light beam ILB, and an image generator 116 including intensity and/or spectral modulator 117 (hereinafter intensity modulator 117) and an image scanner 118 located in the optical path of the light beam LB. The intensity modulator 117 is adapted for modulating the intensity of the light beam in accordance with the intensity of the projected pixel(s) of the image 12. In embodiments in which colorful image projection on the retina is sought, the light module may include one or more light sources (typically three Red, Green and Blue laser sources). In turn, the intensity modulator 117 may be configured and operable to controllably adjust (attenuate/modulate) the intensity Int and possibly also the chromatic/spectral content SPC of the light beam ILB from the light module 114. In various embodiments the intensity modulators/attenuators may be implemented utilizing controllable filters/attenuators located in the optical path of the light beam(s) outputted from the one or more light sources of the light module 114. Additionally or alternatively, the intensity modulators/attenuators may be implemented utilizing spatial light modulators (SLM). Yet, additionally or alternatively, the intensity modulators may be implemented utilizing controllers adapted to control operation of the light sources/lasers in the light module 114 so as to adjust their output intensity. The configuration and/or functional operation of the image projection system 110 according to some embodiments of the present invention is described in more detail with reference to FIGS. 2A to 4 below.

The image scanner 118, located in the optical path of the light beam, may include one or more optical deflectors (e.g. adjustable optical deflectors such as fast scanning/raster mirror(s), and/or a plurality of static elements such as micro-lens array (MLA) or micro-mirror array (MMA)), which are located in the optical path of the light beam LB and configured and operable to perform image scan and/or spatial modulation to deflect the light beam to propagate along various scan/projection angles $\alpha_{scn}$ thereby splitting the light beam to plurality of light beam portions corresponding to respective pixels of the image 12.

The image projection system 110 also includes an image projection controller 112 which is connectable to the image scanner 118 and to the intensity modulator module 117 and configured and operable to obtain image data 12 indicative of image pixels to be projected onto the retina, and operate the image scanner 118 and the intensity modulator 117 to direct the portions of the light beam (spatial/temporal portions of the light beam) towards various scan/output angles $\alpha_{scn}$ with appropriate respective intensities corresponding to the image pixels. In turn, the eye projection optics 130 is adapted for receiving light beams (or portions thereof) outputted from the image generator 116 with the projection angles $\alpha_{scn}$ and direct them such that they are incident on the eye pupil with the corresponding pupil incidence angles $\alpha_{in}$, such that the image pixels are directly projected on the retina in their proper location. The eye projection optics 130 may also be configured and operable for compensating for different gaze directions β of the eye for projecting images on fixed locations on the retina.

The eye projection optics 130, typically includes a angular beam relay module 134, which is adapted to relay the light beam for directing it to be incident onto a pupil EP of a user's eye with appropriate pupil incidence angle $\alpha_{in}$ corresponding to the respective location of the corresponding pixel in the image to thereby enable focusing of the light beam by the eye-lens EL onto a proper location at the eye retina ER on which the image pixel associated with projection angle $\alpha_{scn}$ should be projected. This facilitates direct projection of the image 12 onto the eye retina ER.

According to some embodiments of the present invention the eye projection system 100 also includes a gaze tracking controller 120, which is configured and operable for adjusting/controlling the operations of the eye projection optics 130 and/or of the image projection system 110 in accordance with a gaze direction β of the eye, so as to direct the projections of images onto the retina ER in accordance with the pupil's location and its line of sight when at different gaze directions. More specifically, in some embodiments of the present invention the gaze tracking controller 120 is configured and operable in accordance with any one of Eq. (2) to (4) above for controlling the optical function $F'_{opt}$ of the eye projection optics 130 to enable the image pixels projections on fixed locations on the retina while the gaze changes. It should be noted that when operating according to Eq. (2) above, only the optical function $F'_{opt}$ of the eye projection optics 130 is used/adjusted to compensate for the changes in the gaze direction. However when operating in accordance with Eq. (4) both the optical function $F'_{opt}$ of the eye projection optics 130 and the image scanning function S' of the image projection system 110 (S' being associated with the intensity of which pixel of the image is projected at each projection angle $\alpha_{scn}$ of the image scanner) are adjusted to carry out such compensation.

In this connection it should be noted that the gaze tracking controller 120 may be an electronic/processing module configured and operable for receiving data/signals 22 indicative of the gaze direction β of the eye from a gaze tracking module 20. The gaze tracking module may be included as a part of the system 100 of the present invention or it may be an external system connected thereto. The gaze tracking system may be configured and operable in accordance with any suitable technique for determining a line of sight/gaze direction to which the eye is directed. There are several such known in the art techniques, which can be incorporated in or used in conjunction with the system 100 of the present invention. Such techniques are disclosed for example in International patent application publication WO 2013/117999, U.S. Pat. No. 7,542,210, and U.S. Pat. No. 6,943,754.

Turning back to the eye projection optics 130, according to certain embodiments of the present invention it is configured to have an adjustable optical function $F'_{opt}$ enabling at least partial compensation for changes in the gaze direction. It is noted that when the gaze direction changes, both the location of the pupil and the line of sight of the eye are changed. To this end, the eye projection optics 130 is configured to enable change in the optical path of the light beam LB from the image projection system 110 (e.g. from the image scanner 118) so it can be directed towards the various possible locations of the pupil when at different gaze directions of the eye. Additionally, in certain embodiments of the invention, the eye projection optics 130 is also configured such that modifications of the optical path of the light beam LB, not only direct the light to the respective location of the pupil corresponding to the gaze direction, but also at least partially compensates for the change in the line of sight LOS direction of the pupil at the different gaze directions. For example, for various gaze directions β, the optical function $F'_{opt}$ is adjusted to direct the light beam towards the location of the pupil, while ensuring that the light beam incidents on the pupil with a pupil incident angle $\alpha_{in}$ with respect to the line of sight LOS of the eye at the respective gaze direction β, where the pupil incident angle $\alpha_{in}$ is preserved as a predetermined function (typically a certain monotonic function) of the projection angle $\alpha_{scn}$. This provides direct projection of image pixels onto respective fixed locations on the retina. This feature of the invention is illustrated and exemplified in more detail in FIGS. 2A and 2B.

Figure 2A:
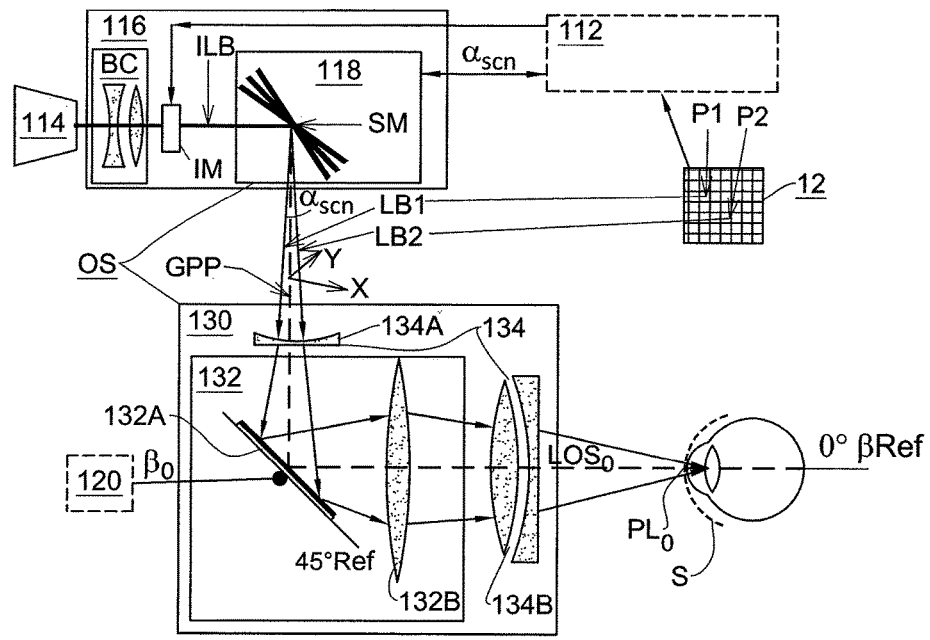
FIGS. 2A and 2B schematically illustrating an optical configuration of the eye projection system 100 according to an embodiment of the present invention, and its operation in two different gaze directions $\beta_0$ and $\beta_1$ of the eye.
Figure 2B:
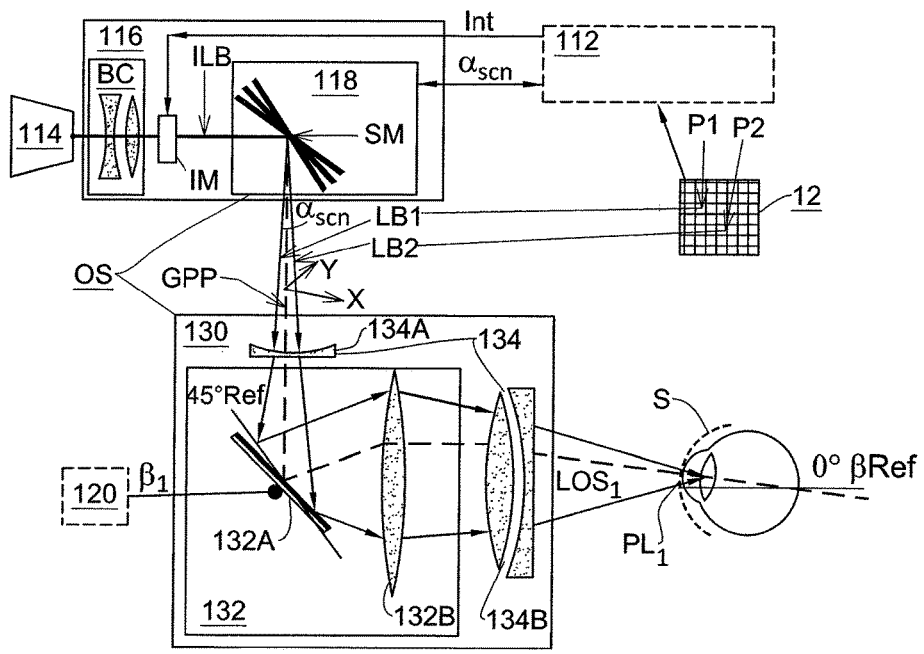

Reference is made together to FIGS. 2A and 2B schematically illustrating an optical configuration of the eye projection system 100 according to some embodiments of the present invention. Particularly shown in these figures, is an example configuration of an eye projection optics 130 of the present invention and its operation (optical function $F'_{opt}$) in two different gaze directions $β_0$ and $β_1$ of the eye.

In this example, the eye projection optics 130 includes a gaze tracking deflector module 132 and an angular beam relay module 134. The gaze tracking deflector module 132 is adapted for deflecting the optical propagation path general light propagation path GPP of the light beam towards the eye, in accordance with the gaze direction β of the eye (namely in accordance with the direction of the eye's line of sight direction of the eye and the pupil's location in different gaze directions). The angular beam relay module 134 is an optical system configured to relay the light beam outputted from the from the image scanner 118 with output projection angle $\alpha_{scn}$ and direct it to be incident onto a pupil EP of a user's eye with appropriate pupil incidence angle $\alpha_{in}$.

As shown in the figures, an input light beam ILB is produced by a light source 112, and its intensity and possibly also its spectral content are adjusted (modulated/attenuated) in accordance with the data of one or more pixels in the image 12. To this end, image generator 116, including for example one or more intensity modulators 117 in the optical path of the light beam ILB, is operated in accordance with the pixels data to control the intensity and/or chromatic content of the pixels image. The light beam is then directed to an image scanner 118.

In the present example the image scanner 118, includes one or more scanning mirrors SM, which perform scanning/raster-scanning of the light beam (e.g. by rotating the mirrors), during which the light beam is deflected to propagate over a range of image projection angles $\alpha_{scn}$ (measured with respect to the general light propagation path GPP), where typically each projection angle corresponds to a pixel of image 12 projected on the retina. The scanning/raster-scanning mirror(s)/deflectors may be implemented utilizing any suitable technique, for example electro optical deflectors and/or using mirrors. such as Micro Electro Mechanical System (MEMS) mirrors mechanically coupled to suitable actuators, such as Piezo-electrical actuators or other types of actuators, enabling the mirrors to deflect a light beam from light module 114 to perform an image/raster scan of the light beam across a range of projection angles $\alpha_{scn}$. As indicated above, an image projection angle $\alpha_{scn}$ may designate a two dimensional value $\{\alpha^X_{scn}\ \alpha^Y_{scn}\}$ corresponding to the horizontal and vertical image projection angles. For example, the angles $\{\alpha^X_{scn}\ \alpha^Y_{scn}\}$ may respectively correspond to the angles between the general light propagation path GPP and the light beam's projections on two planes spanned by the general light propagation path GPP and two lateral axes X and Y orthogonal to the light propagation path GPP. In this connection, it should be understood that although in FIGS. 2A and 2B, for clarity only, a single scanning mirror SM (e.g. fast scanning mirror) is illustrated (e.g. being gimbaled for rotation in two dimensions/axes), in other embodiments of the present invention two or more mirrors/deflectors may be used to deflect the light beam in the two dimensional image projection angles $\alpha_{scn}$ (i.e. $\{\alpha^X_{scn}\ \alpha^Y_{scn}\}$).

Two light beam portions LB1 and LB2 are illustrated in the FIGS. 2A and 2B deflected from the image scanner in two different image projection angles $\alpha_{scn1}$ and $\alpha_{scn2}$. The propagation of these beams through the eye projection optics 130 is exemplified and illustrated in the figure. The angular beam relay module 134 includes two or more optical modules, here first and second optical modules 134A and 134B, which are arranged along an optical path from the image scanner to the eye and configured to direct the light beam to be projected on the pupil with pupil incident angles $\alpha_{in}$ (here $\alpha_{in1}$ and $\alpha_{in2}$ of beams LB1 and LB2 respectively) corresponding to the image projection angles $\alpha_{scn}$ ($\alpha_{scn1}$ and $\alpha_{scn2}$). This is achieved according to certain embodiments of the present invention by utilizing first and second optical modules 134A and 134B having optical powers (respectively associated with first and second focal lengths), and arranging the first and second optical modules 134A and 134B such that they are spaced apart from one another along the optical path of the light LB1 and LB2 propagating from the image scanner to the pupil by an optical distance that substantially equals a sum of said first and second focal lengths. To this end the angular beam relay 134 provides monotonic functional correspondence between the image projection angles $\alpha_{scn}$ at which the light beam portions (e.g. LB1 and LB2) are deflected from the image scanner, and the angles of pupil incidence $\alpha_{scn}$ at which they impinge on the pupil. This provides for the directed imaging on the retina of the eye. It should be noted that in other embodiments of the present invention the same functional operation of the angular beam relay module 134 may be achieved by utilizing/including additional optical modules in the angular beam relay 134, which may have different relations between their optical powers (focal lengths) and their arrangement in the optical path. A person of ordinary skills in the art will readily appreciate how to implement such an angular beam relay module using the configuration exemplified here, or a different configuration. It should also be noted that the optical modules (e.g. 134A and 134B) of the angular beam relay 134 may include one or more optical elements which may also be functional elements integrated with other optical elements of the system 100.

The gaze tracking deflector module 132 is connectable to the gaze tracking controller 120 for receiving therefrom signals/data indicative of the gaze direction of the eye β. The gaze tracking deflector module 132 and is operable for deflecting an optical propagation path of the light beam LB in accordance with signals/data (e.g. operating signals) from the gaze tracking controller 120, for changing/adjusting the optical function $F'_{opt}$ of the eye projection optics 130 in accordance with the gaze direction β of the eye. As indicated above, the gaze tracking controller 120 may be configured and operable in accordance with Eq. (2) or (4) for controlling the gaze tracking deflector 132 state (deflection operation/direction) so as to fully (eq. (2)) or at least partially (e.g. eq. 4) compensate for a shift in the gaze direction β of the eye from the nominal gaze direction (indicated in the figures by 0° β-Ref). In the latter case, additional and complementary compensation may be provided by the image scanning function S' as indicated above and will be discussed in more detail below.

FIGS. 2A and 2B each show schematic illustration of the optical path of two light beams LB1 and LB2, corresponding to two different pixels of the image 12. FIGS. 2A and 2B show the operation of system 100 and particularly of the gaze tracking deflector module 132 thereof in two different gaze states/directions $β_0$ and $β_1$ of the eye respectively. As illustrated, in the different gaze states $β_0$ and $β_1$ the pupil is located in respectively two different pupil locations $PL_0$ and $PL_1$ on a virtual surface S (being a portion of a substantially spherical virtual surface) defining the possible locations of the pupil when eye gazes at different directions, and two different line of sights $LOS_0$ and $LOS_1$ of the eye in the different gaze directions. According to some embodiments of the present invention, the gaze tracking deflector module 132 includes two or more optical elements/modules that are adapted for compensating for both the shift in the pupil's location and the shift in line of sight of the eye associated with different gaze directions.

For example, as illustrated in FIGS. 2A and 2B, the gaze tracking deflector module 132 includes: an adjustable/addressable optical deflector 132A (e.g. being an addressable gaze tracking mirror) and a field selector optical module 132B which are configured and operable together for controlling the propagation of light beams LB (e.g. LB1 and LB2 in the figures) of different image pixels to intersect with the respective locations of the pupil ($LP_0$, and $LP_1$ in the figures) when it gazes in different directions, and also to adjusting the pupil incidence angles of the light beam LB on the pupil (here $\alpha_{in1}$ and $\alpha_{in2}$ of beams LB1 and LB2 respectively) with respect to the lines of sight LOS (here $LOS_0$ and $LOS_1$ correspond to two different gaze directions) such that the incidence angles $\alpha_{in}$ remain fixed with respect to the line of sight LOS of the eye and are invariant to changes in the line of sight LOS direction of the eye/pupil.

The adjustable/addressable optical deflector 132A is addressable in the sense that it is responsive to input signals indicative of the gaze direction (or signals indicating the address/orientation angle of the deflector 132A corresponding to the gaze direction β) and is operable/shiftable for adjusting its orientation angle/deflection angle respectively so as to deflect the light beam LB to propagate along a respective optical path corresponding to the gaze direction β. The field selector optical module 132B is configured and operable to receive beams LB of light propagating along various respective optical paths corresponding to different gaze directions and direct them to the corresponding location of the pupil at the respective gaze directions, to incidence on the pupil with the appropriate incidence angles.

According to certain embodiments of the present invention the adjustable/addressable optical deflector 132A is located in between the first and second optical modules 134A and 134B of the angular beam relay module, along the general light propagation optical path GPP of path of the light beams LB (e.g. LB1 and LB2) from the image scanner 118. The field selector optical module 132B of the gaze tracking deflector module 132 may be located along the optical path GPP downstream from the adjustable/addressable optical deflector 132A with respect to the light propagation direction. The field selector optical module 132B may be located before or after the second optical module 134B of the angular beam relay 134, and/or it may be integrated therewith to form an integral optical component performing the functions of both the field selector 132B and the second optical module 134B of the angular beam relay 134. The field selector optical module 132B may include an a-spherical lens and/or mirror. In FIGS. 2A and 2B the field selector optical module 132B is implemented by a set of two lenses arranged to receive the light beam from the gaze tracking addressable optical deflector 132A and direct them to the pupil. Yet, as further illustrated in the example of FIG. 5, the field selector may be implemented as a reflective/semi-reflective-beam-splitting surface/coating. For example it may include an off-axis parabolic deflector, which may be associated with an eyeglasses lens of eye glasses implementing the system 100 of the present invention.

It should be noted that according to some embodiments of the present invention the image is directly projected on a specific/fixed location on the retina, while without placing any adjustable/movable optical elements in the field of view of the user in front of the eye. To this end, the gaze tracking addressable optical deflector 132A and also image scanner mirror SM may be located at a region aside from the eye, outside the field of view of the user, while the angular beam relay module (which may be include fixed optical elements, may be configured to properly directing the light beam from the image projection system towards the pupil's location.

The two light beams (i.e. light beam portions) LB1 and LB2 illustrated in FIG. 2B are associated with the projections of two respective pixels P1 and P2 of image 12 on the retina. Image projection controller 112 may be adapted for receiving the image data 12, operating the image generator 116 for generating the light beams LB1 and LB2 with appropriate intensities (e.g. and chromatic content) corresponding to the data of the respective pixels P1 and P2, and operating the image scanner 118 to direct/deflect the respective light beams LB1 and LB2 to appropriate respective image projection angles ($\alpha_{scn1}$ and $\alpha_{scn2}$) associated with the locations of the respective pixels P1 and P2 in the image 12. To this end, the eye projection optics 130 obtains data indicative of the gaze direction β from controller 120, and adjusts the angular position/deflection-state of the gaze tracking deflector module 132 so as to relay each of the light beams LB1 and LB2 to be incident on the pupil at the appropriate pupil location ($PL_0$ and $PL_1$ in FIGS. 2A and 2B respectively), and with the appropriate pupil incidence angles ($\alpha_{in1}$ and $\alpha_{in2}$ of light beams LB1 and LB2 respectively) with respect to the line of sight axis/direction of the eye ($LOS_0$ and $LOS_1$ in FIGS. 2A and 2B respectively). In the illustration of FIGS. 2A and 2B, similar light beams, LB1 and LB2, are illustrated, deflected to similar respective projection angles ($\alpha_{scn1}$ and $\alpha_{scn2}$) by the image scanner. The eye gaze directions $β_0$ and $β_1$ are different in FIGS. 2A and 2B, and accordingly, the angular position of the addressable mirror/deflector 134A is adjusted to direct the light beams towards the pupil location to be incident on the pupil with the respective appropriate incidence angles $\alpha_{in1}$ and $\alpha_{in2}$. Although not specifically designated in the figure, the incidence angles of the beams $\alpha_{in1}$ and $\alpha_{in2}$ with respect the pupil's lines of sight $LOS_0$ and $LOS_1$ are similar in both the figures and correspond respectively to the locations of the respective image pixels P1 and P2 associated with these light beams.

It should be understood that although the beams LB1 and LB2 are illustrated together in the figures, they do not necessarily co-exist/are projected together. In fact, typically in the embodiment of the present invention such as those of FIG. 1 and FIGS. 2A and 2B, wherein an image scanner is used, typically each beam is associated with a particular location of the scanning mirror/deflector SM of image scanner 118, and thus the beams LB1 and LB2 do not co-exist.

It should be noted that for certain embodiments of the present invention there may be a significant advantage for utilizing scanning projection system, such as that described with reference to FIGS. 2A and 2B above. This is particularly because utilizing such scanning projection system for compact applications, such as for eye glasses applications, may provide for projecting images on the retina with better image quality than what can be achieved when area projection systems are used (e.g. such as that disclosed in FIGS. 2C and 2D). To this end, scanning projection systems may be more compact then corresponding area projection systems. Also utilizing scanning projection system, in which the image is projected to the eye by utilizing a laser beam for projecting a pixel at a time, provides no crosstalk between adjacent pixels. Additionally, the pixel size, namely the width of the light beam portion (e.g. LB1 or LB2) associated with each specific pixel projection, may be substantially wider (typically by one or more orders of magnitudes) than what is achievable when using the aerial image projection technique in compact systems. Accordingly, optical modules of the eye projection optics 130 and particularly of the angular beam relay module 134, may be configured with lower numerical apertures and thus be associated with lower optical aberrations and provide high quality image relay to the eye with good modulation transfer function (MTF). This facilitates use of compact image projection system for projecting images with improved dynamic range, high image contrast, and high resolution and brightness on the eye retina. Additionally, utilizing scanning projections in compact application, may also reduce and/or entirely eliminate diffraction artifact which may be produced by compact aerial projection systems due to the significantly smaller pixels sizes in the later deteriorated.

However, it should also be noted that in some embodiments of the present invention, and specifically for non-compact system, an aerial image projection system may be used instead of the scanning image projection. To this end, instead of the scanning mirror/deflector SM, image scanner 118 may include a spatial light modulator (SLM) such as liquid crystal modulator, which may be adapted for simultaneously modulating and directing a plurality of light beams associated with a plurality of pixels.

Figure 2C:
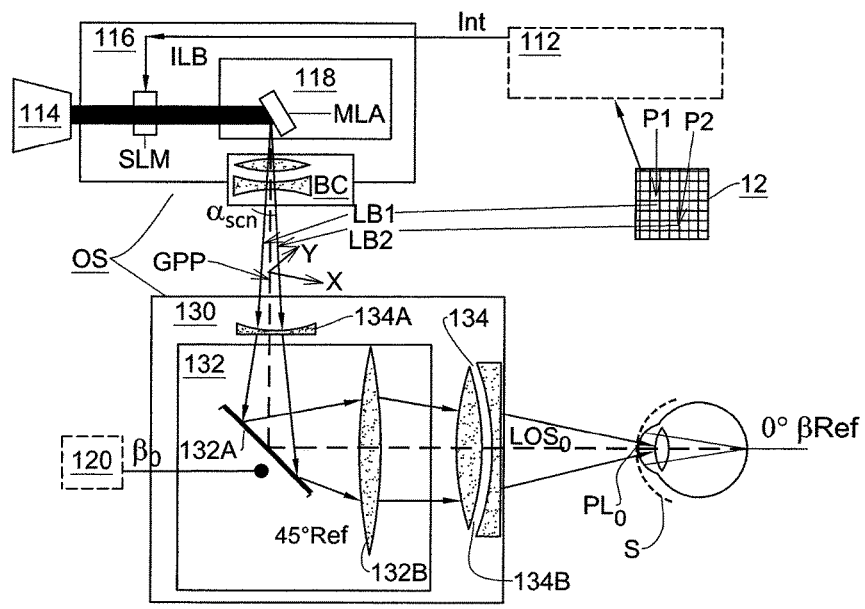
FIGS. 2C and 2D schematically illustrating an optical configuration of the eye projection system 100 according to another embodiment of the invention and its operation in two different gaze directions $\beta_0$ and $\beta_1$.
Figure 2D:
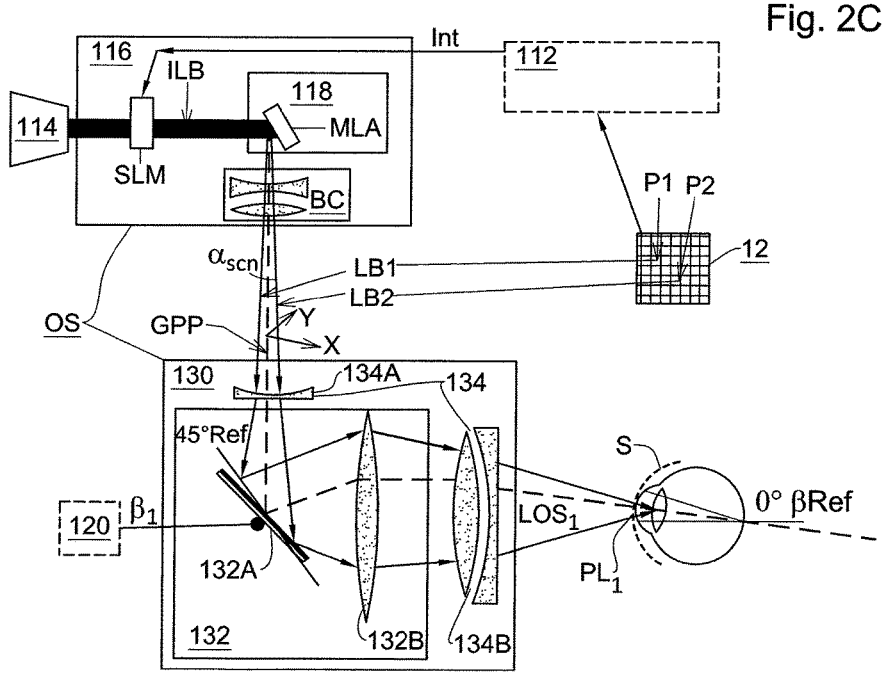

Reference is made to FIGS. 2C and 2D illustrating an optical configuration of an eye projection system 100 according to another embodiment of the present invention, in which some or all of the light beams associated with the image pixels (e.g. in the figure, light beams LB1 and LB2 associated with pixels P1 and P2, are concurrently generated and concurrently directed with the respective projection angles ($\alpha_{scn1}$ and $\alpha_{scn2}$) towards the eye projection optics 130. The eye projection optics 130 projects the light beams with the respective projection angles ($\alpha_{scn1}$ and $\alpha_{scn2}$) onto the pupil with corresponding pupil incidence angles ($\alpha_{in1}$ and $\alpha_{in2}$) so as to generate/project the image 12 onto the eye retina. The configuration of system 100 in FIGS. 2C and 2D is similar to that illustrated in FIGS. 2A and 2B and described in detail above, except that here a plurality of light beams corresponding to the plurality of image pixels, are concurrently directed to the pupil. To this end, the image generator 116 may include for example one or more spatial light/intensity modulators SLMs in the optical path of the light beam ILB. Spatial light modulators SLMs are capable of independently modulating the intensities of different spatial portions of the input light beam ILB. e.g. instead of or in addition to the intensity modulators IM illustrated in FIGS. 2A and 2B, here the SLM provides for concurrently adjusting the intensity of light beams/portions associated with different pixels. In turn, the image scanner 118 includes an optical module, which is capable of receiving the light beam portions outputted from the SLM and directing each portion (e.g. light beams/beam-portions LB1 and LB2) to propagate towards the eye projection optics 130 with appropriate projection angle corresponding to respective pixel of the image with which the beam portion is associated.

For example, in some embodiments of the present invention, the SLM may include for example a liquid crystal intensity modulator, divided into a matrix of a plurality of cells, each associated with the attenuation of the intensity and/or with control of the chromatic contents of one of the beams (e.g. one of LB1 and LB2) that are associated with different image pixels. Optionally, a matrix of a micro lens array may be arranged in the optical the liquid crystal intensity modulator, to receive the light beams (e.g. LB1 and LB2) outputted therefrom and direct them with corresponding image projection angles (e.g. $\alpha_{scn1}$ and $\alpha_{scn2}$ to the gaze tracking optical module 130).

To this end, instead of an image raster scan mirror, such as the SM mirror of FIGS. 2A and 2B, here a static optical module may be used. For example a micro-lens array MLA may be arranged in the optical path of the SLM and be configured to directing pixel related light beams which are emitted from each cell in the SLM towards appropriate projection angles. The spatial light modulator SLM is located in the optical path of the input light beam ILB and is adapted to receive the input light beam and ILB and produce therefrom a plurality of light beams (e.g. LB1 and LB2), whose intensities (and possibly also chromatic content) correspond to these values in the respective image pixels (e.g. P1 and P2) of the image 12. The static optical module of the image scanner 118, which is herein exemplified as MLA, is configured and operable to receive the plurality of light beams from the image generator 116 (from the SLM) and direct these light beams to respective output angles (referred to above as image projection angles (e.g. $\alpha_{scn1}$ and $\alpha_{scn2}$) associated with the locations of the respective pixels (P1 and P2) in the image 12 and their designated projection locations on the retina. To this end, as in the embodiment of FIGS. 2A and 2B, also in the embodiment of FIGS. 2C and 2D the eye projection optics 130 relays each of the light beams (LB1 and LB2) to be incident on the pupil at the appropriate location of the pupil (PL$_0$ and PL$_1$ in FIGS. 2C and 2D respectively), and with the appropriate pupil incidence angles ($\alpha_{in1}$ and $\alpha_{in2}$ of light beams LB1 and LB2 respectively). Thus, in the embodiment of FIGS. 2C and 2D the plurality of light beams associated with the different image pixels are concurrently generated utilizing an SLM and are directed, utilizing a static optical module such as an MLA, towards the eye projection optics 130.

In the configuration of FIGS. 2C and 2D the gaze tracking optical module 130 is configured such that the operation and angular deflection position/state of the gaze tracking addressable optical deflector 132A is determined, based on the gaze direction β and independent of the specific pixel which is projected on the retina. Accordingly, in such embodiments, the plurality of pixels can be projected on the retina simultaneously. It should be understood that this requirement is not necessary in optical configurations of the system in which the pixel related light beams are not projected concurrently onto the eye (as in the configuration of FIGS. 2A and 2B). In such cases, angular deflection position/state of the gaze tracking addressable optical deflector 132A may be determined based on both the gaze direction β and the specific pixel (e.g. specific projection angle $\alpha_{scn1}$) of the beam (e.g. LB1) that incident the gaze tracking addressable optical deflector 132A at any particular moment.

Thus, illustrated in FIGS. 2A to 2D is the optical configuration and operation of eye projection system 100 configured to an embodiment of the present invention for projecting images on a retina of an eye. The eye projection system includes a light module 114 and an image generator 116 producing an input light beam ILB of controllable intensity, and an optical system OS arranged in an optical path of the input light beam. The optical system includes first and second two-dimensional optical deflectors. The first optical deflector being associated with the image scanner 118, and may be implemented as one or more scanning deflectors/mirrors SM (e.g. fast scanning mirror) configured for performing image/raster scan of the light beam LB to segment the light beam into temporal portions or as an MLA or MMA module configured for segmenting the light beam into spatial portions. The image scanner 118 is configured to deflect the spatial and/or temporal portions of the light towards different projection angles associated with the different respective image pixels. The second optical deflector being an adjustable/addressable optical deflector 132A, is associated with the gaze tracking deflector module 132, which can be implemented as an addressable mirror for tracking the location of the pupil in different gaze states. The adjustable/addressable optical deflector 132A may be implemented utilizing any suitable technique, for example it may include an electro optical deflector and MEMS mirrors which can be actuated. It should be noted that typically, the gaze tracking deflector module 132 is configured and operable for compensating over two dimensional shifts $\{\beta^x \beta^y\}$ in the gaze direction β. Accordingly the adjustable/addressable optical deflector 132A is typically implemented utilizing at least one optical deflector which can be actuated and which is addressable to different angular directions spanning certain a two dimensional solid angle (e.g. cone-like solid angle) with respect to the optical path. Alternatively, or additionally the adjustable/addressable optical deflector 132A may be implemented utilizing two or more mirrors rotatable with respect to the optical path about two or more different lateral axes.

The gaze tracking controller 120 and the image projection controller 112 may be implemented by a single control module/unit or by separate two or more control units. As will be readily appreciated by those versed in the art, the controller(s) may be implemented analogically, utilizing suitable analogue circuits, or digitally by utilizing suitable processor(s) and memory/storage module(s) carrying suitable soft-/hard-coded computer readable/executable instructions for controlling the operations of the gaze tracking deflector 132A and for controlling the operation of the an image generator 116 and possibly also the operation of the image scanner 118 for generating light beams of suitable intensities, and directing them to proper image projection angles in accordance with the image data. To this end, the controller(s) is/are adapted to receive data indicative of an image 12 to be projected onto a retina of the eye, and data indicative of a gaze direction β of the eye, and projecting pixels of the image onto corresponding locations on the retina by carrying out the operations of method 200 in the following, for projecting each pixel of the image.

As indicated above, according to some embodiments of the present invention the eye projection system 100 may be adapted to direct substantially collimated light beams towards the pupil so that the eye perceives these light beams as being originated from an image plane located at an infinite distance from the eye. To this end, in some variants of the present invention the light module 114 may be adapted to provide coherent light and may for example include one or more lasers for generating the input light beam ILB.

Additionally, or alternatively, the system 100 may include one or more to beam collimators BC, which may include or more optical elements arranged along the optical path of the light beam(s) (e.g. ILB and/or LB). For example, in the embodiment of FIGS. 2A and 2B, the beam collimator BC is presented in the optical path of the input light beam ILB. Alternatively or additionally, in example of FIGS. 2C and 2D, one or more beam collimators BC are illustrated in the optical path of the light beam LB propagating from the image scanner 118 towards the gaze deflection optical module 130.

According to some embodiments of the present invention the beam collimators are adapted for controlling a degree of collimation of the light beam LB that incident on the pupil. Specifically, in certain embodiments the beam collimators are configured and operable for collimating the light beam LB such that it is substantially collimated when incident on the pupil. Accordingly, the eye perceives the image projected on the retina as being originated from an infinitely distant image plane. This enable the direct projection of the image on the retina, while relaxing the focusing requirements from the eye lens and thus providing for relieving eye fatigue and/or headaches which may be associated with projecting the eye with images perceived to be located at finite distances from the eye.

Alternatively or additionally, the beam collimator(s) BC or other optical modules of system 100 may be configured and operable for adjusting the width of the light beam that is incident LB on the pupil. In many cases it may be desired that at the location of the pupil the beam width is substantially narrower than the pupil's diameter. This provides for extending the depth of field (depth of focus) of the image projection on the retina thus provide an alternative or an additional ways for reducing eye fatigue associated the eye lens focus. In this connection it should be understood that this option of utilizing the narrow beam width for extending the depth of field of the image projection on the retina, may be used for reducing eye fatigue also in embodiments where the light beams directed to the pupil are not collimated.

Reference is made to FIG. 3 which is a flowchart 200 showing a method according to the present invention for projecting images on an eye retina. The method may be implemented by one or more controllers of an eye projection system 100 configured according to an embodiment of the present invention. Operations 210 to 250, are generally carried out for each of the pixels $\{P_i\}$ in the image 12. These operations may be carried out sequentially for each pixel, when operating in image scanning mode, in accordance with the configuration of FIGS. 2A and 2B in which the image pixels are projected sequentially. Alternatively or additionally, these operations may be performed concurrently for all, or for a plurality of pixels, in embodiments such as in FIGS. 2C and 2D, where the image pixels are concurrently projected onto the retina (e.g., embodiments in which the intensity and special/angular distribution of light beams which relate to different image pixel are concurrently managed by an SLM and a properly configured optical module (such as MLA) of the image scanner 118.

In operation 210 data indicative of a gaze direction β of the eye is obtained from a gaze tracking module which is configured and operable for determining the gaze direction of the eye.

In operation 220, the projection angle of the image scanner 118 is determined. In this connection, in cases where the image scanner 118 includes a scanning mirror/deflector configured/actuated for performing an image/raster scan, the instantaneous projection angle $\alpha_{scn}$ (e.g. $\{\alpha^X_{scn}, \alpha^Y_{scn}\}$) may be obtained/determined. Alternatively, in cases where the image scanner is configured for applying spatial modulation to the input light beam ILB (to apply different intensity/chromatic modulation to spatial portions of the input light beam ILB associated with different pixels), then the projection angle $\alpha_{scn}$ being the output angle from each specific spatial cell of the SLM, is obtained.

Operation 230 is carried out to determine the intensity and possibly also the chromatic content of the image pixel Pi which is to be projected onto the retina via the respective projection angle $\alpha_{scn}$. To this end, in 232 an image mapping, such as S' or S discussed above with reference to Eqs. (1), (3) and (4) above may be used. The image mapping S' or S may be implemented as functions or lookup data tables (LUTs) associating each projection angle $\alpha_{scn}$ with a corresponding pixel $P_i$ or pixel location in the input image 12. As indicated above with reference to Eqs. (3) and (4) image mapping S' may be used to partially or entirely compensate for the changes in the gaze direction β.

In such cases the image mapping S' may associate each given gaze direction β and given projection angle $\alpha_{scn}$ with a corresponding pixel Pi in the image. As indicated above, utilizing the image mapping S' to compensate for different gaze directions, may be less desirable in certain implementations of the system, as it might require using projecting the eye with light beams wider than the pupil's diameter, thereby impairing the achievable depth of field of the image projection on the retina. Additionally, using this technique may in some cases be limited to only partial compensation of the gaze direction β because it requires that the gaze tracking optical system 130 which directs the light beams to the eye, will support an extended angular range of light beams propagation to the eye (to cover the angular range the line of sight LOS that the eye may require which may be about a solid angle of Ω=~60°. This, on the one hand requires complicated optics which may not be feasible on some systems and on the other hand, it may be wasteful in terms of SLM real-estate in embodiments where SLM is used, or wasteful in terms of the angular resolution of the MLA or scanning/steering mirror, in cases where any one of these is used in the image generator 116. To this end, in certain embodiments of the present invention it is preferred to use the gaze tracking addressable optical deflector 132A of the gaze tracking optical module 130 for entirely compensating for the total gaze direction angle β or for compensating for most of the gaze direction by a compensation angle $\beta_1 \sim \beta$ and utilizing the mapping function S' for digitally fine tuning of the gaze direction compensation by the compensation angle $(\beta-\beta_1) \ll \beta$. To this end, the fine tuning compensation angle which is performed digitally by the mapping S' is limited in some embodiments to angles $\beta-\beta_1 \ll \omega$ where ω presenting the solid angle of the field of view of the eye when at a fixed gaze. This allows using the light beam with a beam width smaller than the pupil diameter, thus enabling to achieve image projection onto the retina with extended depth of field of the image.

Thus, in 232 the pixel $P_i$ associated with the projection angle given projection angle $\alpha_{scn}$ is determined by utilizing the trivial image mapping function/LUT S, which incurs no compensation for gaze direction, or by utilizing the compensated image mapping function/LUT S', which incurs at least partial compensation for the gaze direction. Accordingly, in 234, the value of the pixel $P_i$ is determined/retrieved from the image data 12. This may include merely the gray scale intensity value of the pixel and/or the chromatic (e.g. RGB) intensity value of the pixel in case color image projection is sought.

Operation 240 includes adjusting the intensity and/or the chromatic content of the input light beam ILB, or of a respective portion thereof, in accordance with the data of the corresponding pixel $P_i$ determined in 230. In this connection, in embodiments such as that illustrated in FIGS. 2A and 2B (in which for each pixel the entire input light beam is steered to the appropriate projection angle $\alpha_{scn}$ by raster- or scanning-mirrors of the image scanner 118), the intensity of the entire input light beam ILB and/or the intensities of respective chromatic portions of the entire input light beam ILB may be adjusted by utilizing intensity modulators IM in the input path of the input light beam ILB. This is indicated in optional step 242A in the figure. Alternatively or additionally, in embodiments such as illustrated in FIGS. 2C and 2D (in which SLM(s) is/are used to divide and separately control the intensity different spatial portions of the input light beam ILB) the operation of the respective spatial cell of the SLM of the image generator, which corresponds to the projection angle $\alpha_{scn}$, may be controlled to adjust to the intensity and/or chromatic content of the spatial light beam in accordance with these values in the pixel Pi.

In operation 250 the deflection angle of the gaze tracking deflector 132 is adjusted in accordance with the gaze direction β, to direct the light beam associated with the pixel Pi to be incident on the pupil with a pupil incidence angle $\alpha_{in}$ corresponding to the desired location of that pixel on the retina. In this connection, in cases where partial compensation for the gaze direction is performed digitally via the image mapping function/LUT S', the deflection angle of the gaze tracking deflector 132 may be adjusted to provide compensation only for the complementary part $\beta_1$ of the gaze direction β which is not digitally compensated.

Figure 4:
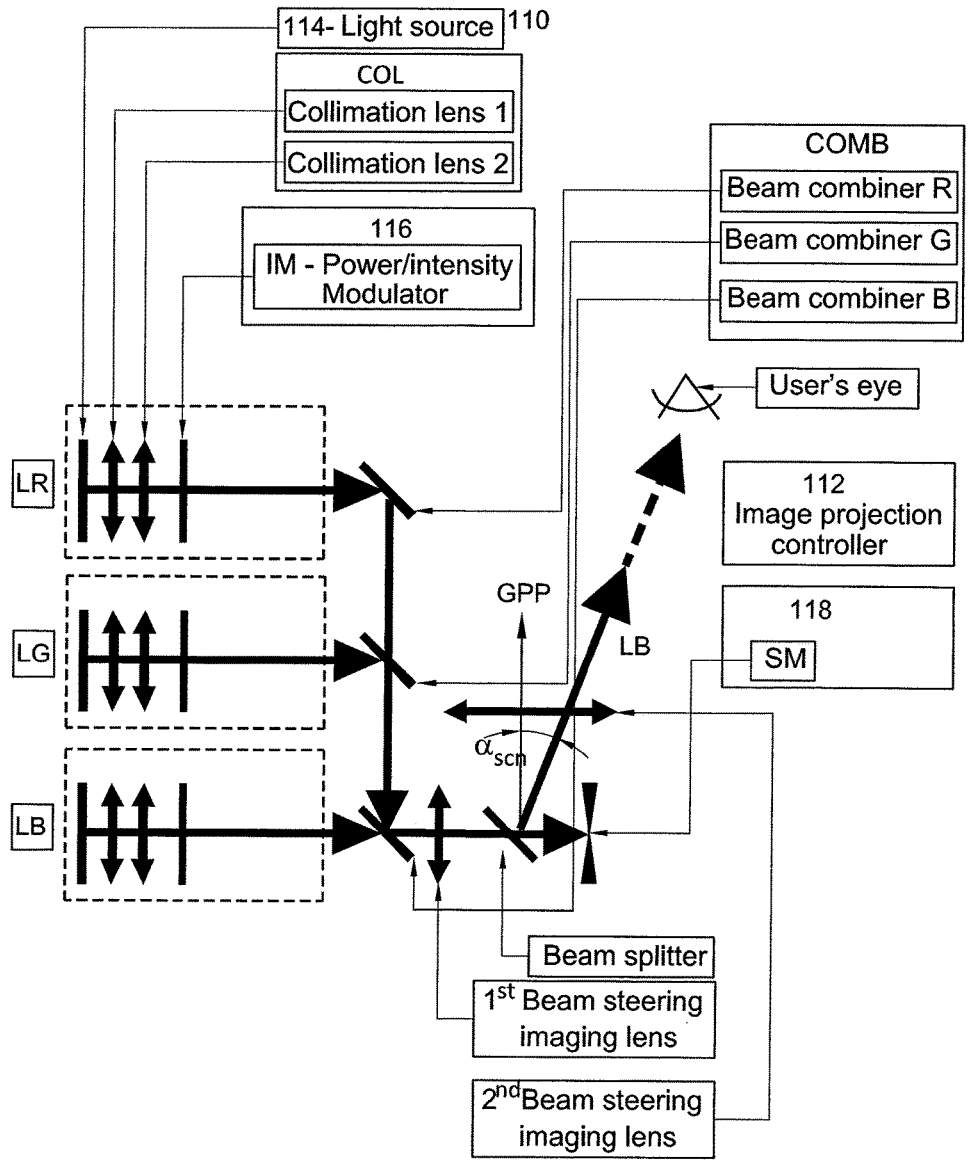
FIG. 4 is a functional block diagram illustrating schematically the configuration of an image projection module 110 according to certain embodiments of the present invention.

Reference is made to FIG. 4 illustrating schematically the configuration of an image projection system/module 110 according to certain embodiments of the present invention. As indicated above, the light module 114 may include one or more light source modules in different colors. In the embodiment illustrated in FIG. 4, three chromatic light modules, LR, LB and LG, which may be Red, Green, and Blue lasers are used to provide RGB light. It should be noted that here RGB light is used only as an example and that light sources/lasers corresponding to other light color pallets may also be used for projecting colorful images on the retina.

As illustrated in a self explanatory way in FIG. 4, the light beams from light modules, LR, LB and LG are combined using beam combiner optics COMP including suitable beam splitter combiners and possibly also optics for directing the beams from light modules, LR, LB and LG to propagate along common general propagation axis GPP. The one or more beam splitter combiners COMP, may include for example spectral/polarization beam splitter/combiner modules arranged along the optical path of the chromatic light beams outputted from the one or more chromatic light modules RL, BL and GL and configured for combining these light beams to propagate as a combined light beam LB. The chromatic content of the combined light beam LB is controlled by the image generation module 116. The latter may, for example, include separate intensity/power modulator(s) IM (and/or separate SLMs) for each color. Typically, at least one intensity/power modulator IM (or SLM) is associated with each one of the chromatic light sources/modules RL, BL and GL.

The image generation module 116 may be configured and operable for controlling the intensity of the light beam of each laser (e.g. by controllably attenuating the light beam outputted from the laser, or by controlling the laser's operation) so as to adjust the chromatic/spectral content of the combined light beam LB.

Figure 5:
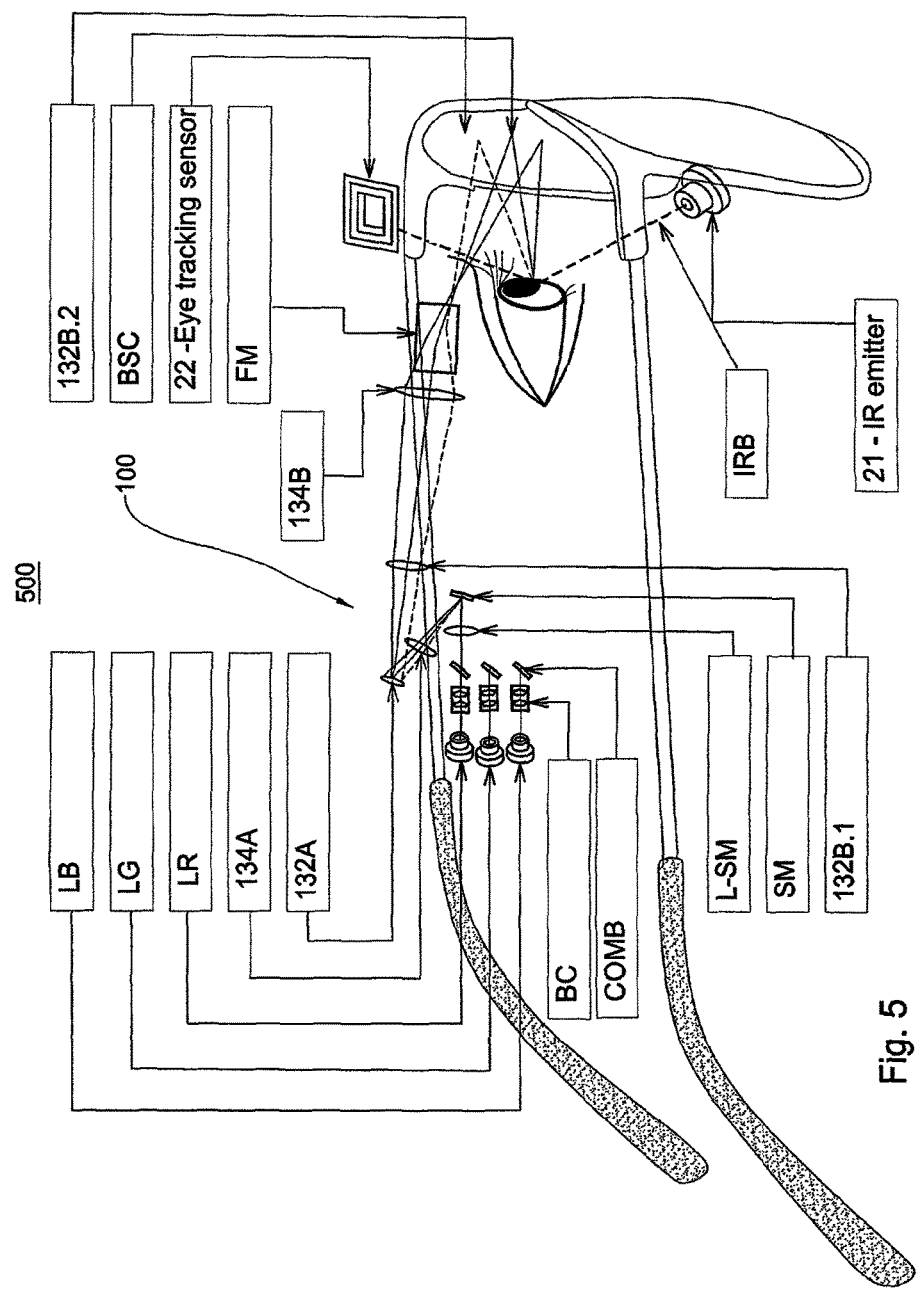
FIG. 5 is a schematic illustration of eye glasses including an eye projection system 100 according to an embodiment of the present invention.

Reference is made to FIG. 5 illustrating in a self explanatory manner an eye glasses 500 configuration including an eye projection system 100 configured and operable as according to an embodiment of the present invention. The eye projection system 100 in this embodiment includes an image projection system/module 110 which is generally furnished at a handle/arm of the eye glasses 500 and includes modules configured and operable similarly to those described above with reference to FIGS. 2A-2B and FIG. 4.

The eye projection system 100 in this embodiment also includes an eye projection optics 130 similar to that described and illustrated above with reference to FIGS. 2A-2B. To this end, the functional operation and configuration of modules 110 and 130 of the eye projection system 100 should not be described here in details except for noting that in this embodiment most of the optical elements of the eye projection system 100 may be furnished on the frame and/or handle of the eye glasses, while the final optical elements, from which the light is projected to the pupil may be incorporated/integrated with the eye-glasses lens. To this end an image or a sequence of video images may be directly projected onto the eye(s).

In this particular embodiment the image projection system includes three light R, G and B, modules, LR, LG and LB associated with respective beam collimators BC and with a beam combiner module COMB combining the light therefrom to propagate along a common path and lens L-SM for directing the combined light beam towards the scanning mirror SM of the image scanner (118 in FIG. 1). The beam relay module 134 includes two lenses 134A and 134B and in the optical path between them located is the gaze tracking addressable optical deflector 132A of the gaze tracking optical module 130. In the present example field selector optical module 132B (in FIG. 2A-2D) is implemented by two optical elements 132B.1 and 132B.2, one 132B.1 being a lens located along the optical path after the gaze tracking addressable optical deflector 132A, and the other 132B.2 being a reflective surface implemented by or on the lens of the eye glasses.

In this regards it should be noted that according to some embodiments of the invention, as illustrated here, directing the image projection to the pupil's location and with the proper incidence angels is achieved without utilizing moving/adjustable optical modules/deflectors in-front of the eye (e.g. in the field of view of the eye). This facilitates esthetic appearance of the device and also eases its use by users since there are no moving/changing elements at the field of view of the eye. Specifically, in the present example, both the gaze tracking addressable optical deflector 132A, and the image scanner mirror SM are located at the arm of the eye glasses frame. A folding mirror FM is used at the edge of the frame/arm to direct the light beams from system 100 to the proper incident on the pupil.

In certain embodiments of the present invention the eye glasses 500 may be configured and operable for projecting pure virtual reality and/or augmented virtual reality to one or both of the user's eyes. In the later case, the eyeglass lens may include a beam splitter combiner surface BSC adapted for reflecting light from the eye projection system 100 towards the user eye and transmitting external light from a scenery towards the user's eye. For example, in some embodiments light module 114 of system 110 may be configured for generating input light beams including one or more narrow spectral bands (e.g. narrow RGB spectral bands) having substantially narrow spectrum. In turn the beam splitter combiner surface of the eye glass lens may configured as a notch filter adapted for reflecting the one or more narrow spectral bands towards the user's eye while transmitting light arriving from the scenery and being outside of these narrow spectral bands. Alternatively or additionally the light beam/light beam portions generated by system 110 may be polarized to a certain polarization, and the beam splitter combiner surface may be configured as a polarizer adapted for reflecting said certain polarization towards the user eye.

It should be noted that although in the figure only one eye projection system 100 is depicted, to such systems may be furnished in the eye glass for projecting images on each of the eyes separately. In such cases common controllers may be used for operation the image projection modules 110 and the eye projection optics 130 of both systems. Also, the systems may be operated to project stereoscopic images/video to the user eyes to produce a 3D illusion.

Also illustrated schematically in FIG. 5 is a gaze eye tracking module (20 in FIG. 1), configured and operable for determining the direction β of the eye gaze and providing data indicative thereof to system 100. The gaze eye tracking module 20 may generally be configured and operable according to any suitable technique know in the art.

In the present example the gaze tracking module includes an infra-red (IR) light emitter 21 furnished on the eye glasses bridge and adapted for directing an IR light beam IRB to the eye, and an eye tracking sensor 22, being an IR sensor, located at on the eye glasses frame/arm and adapted for detecting the reflection of the IR light beam IRB from the eye (e.g. from the pupil and/or cornea and/or retina thereof). A controller (not shown) is adapted for processing the pattern of the reflected IR light beam to determine the gaze direction of the eye.

Thus, the present invention provides novel systems and methods for direct projection of images/video sequences to an eye retina. The direct projection can be implemented example utilizing an angular beam relay module, configured and operable for directing pixel related light beam portions, which are associated with respective pixels of the image, to incident on the eye pupil with respective pupil incidence angle corresponding to the locations of the respective image pixels. The angular beam relay module thus used according to the present invention directly project images onto the eye retina without forming an intermediate image plane at a finite distance outside the eye. In some case the light beam portions are collimated upon incidence on the pupil. Accordingly, the image projected on the retina is perceived by the eye as originating from an infinitely distant image plane. Alternatively or additionally, the images may be projected to the eye by light beam portions light beams with width narrower than the pupil diameter. This provides an extended depth of focus of the image projection on the retina. The features of the invention relating perception of the image projection from infinitely distant intermediate image plane, or to the extended depth of field of the image projection on the retina, provide for reducing and possibly entirely eliminating eye confusion and fatigue which are associated with in direct projection of images to the eye, via an intermediate image plane located at finite distance from the eye. Additionally, the above advantages of the present invention may also be achieved while tracking the gaze direction of the eye/pupil and compensating for changes in the gaze direction, for projecting the images on fixed location on the retina while the gaze direction of the eye may change. As indicated above, this may be achieved utilizing a gaze deflecting optical module, configured and according to the invention to be. adjustable in accordance with the gaze direction of the eye to direct the pixel related light beam portions towards the location of the pupil, with the proper pupil incident angle with respect to the pupil's/eye's line of sight in different gaze directions.

The invention claimed is:

1. An eye projection system comprising:
   an image generator; and
   an eye projection optical module;
   wherein:
   said image generator is adapted to obtain data indicative of an image, produce a plurality of light beam portions corresponding to pixels of said image, adjust the intensity of each light beam portion of said light beam portions in accordance with a value of a pixel of said image corresponding to said light beam portion, and direct said light beam portion to propagate along a general optical propagation path towards said eye projection optical module with a projection angle $\alpha_{scn}$ relative to said general optical propagation path, where projection angle $\alpha_{scn}$ is determined in accordance with a location of said respective pixel in the image; and
   said eye projection optical module comprises a gaze tracking deflector configured and operable to be responsive to input signals indicative of a gaze direction β of a user eye for deflecting the general optical propagation path of the light beam portions towards a pupil of said user eye in accordance with said gaze direction β; and wherein said general optical propagation path is deflected such that the light beam portions incident on the pupil with pupil incidence angles $\alpha_{in}$, corresponding to the projection angles $\alpha_{scn}$, with respect to a line of sight of said pupil associated with said gaze direction β such that the pupil incidence angle $\alpha_{in}$ is a monotonic function of the projection angle $\alpha_{scn}$, thereby directly projecting said image onto a retina of said eye at a substantially fixed location on the retina regardless of said gaze direction β of the eye.

2. The eye projection system of claim 1, further comprising one or more beam collimators adapted for effecting a collimation of said light beam portions such that said light beam portions incident on said pupil while being substantially collimated thereby enabling direct projection of the image on said retina whereby said image is perceived to be originating from an infinite distance from the eye.

3. The eye projection system of claim 1, further comprising one or more optical modules adapted for effecting widths of said light beam portions, such that said the widths is smaller than a diameter of said pupil, thereby enabling projection of said image on the retina with an extended depth of focus.

4. The eye projection system of claim 1, wherein said gaze tracking deflector comprises: an addressable optical deflecting unit located along said general optical propagation path, and a field selector optical module located in said optical path downstream from said addressable optical deflecting unit with respect to a light propagation direction through the system.

5. The eye projection system of claim 4, wherein said addressable optical deflecting unit is responsive to said input signals indicative of said gaze direction β and operable for adjusting a deflection angle thereof to deflect a light beam incident thereon to propagate along a respective optical path corresponding to said gaze direction β; and said field selector optical module is configured and operable to receive beams of light propagating along various respective optical paths corresponding to different gaze directions β and direct them towards corresponding locations of said pupil associated with said different gaze directions β respectively.

6. The eye projection system of claim 5, wherein said field selector optical module comprises a-spherical optics.

7. The eye projection system according to claim 1, wherein the eye projection optical module further comprises an angular beam relay module, which is configured and operable for receiving each light beam portion propagating at various projection angles $\alpha_{scn}$ from the image generator, and relaying said light beam portions to be projected onto the pupil with corresponding pupil incidence angles $\alpha_{in}$; and wherein said gaze tracking deflector comprises an addressable optical deflecting unit located along the general optical propagation path in between optical modules of the angular beam relay module.

8. The eye projection system of claim 7, wherein said angular beam relay module comprises a first optical module and a second optical module respectively associated with first and second focal lengths, the first and second optical modules being spaced apart from one another along said general optical propagation path by an optical distance being substantially equal to a sum of said first and second focal lengths.

9. The eye projection system of claim 1, wherein said gaze tracking deflector comprises a field selector optical module and wherein said second optical module of the angular beam relay and said field selector optical module are integral in a common optical element.

10. The eye projection system according to claim 1 wherein said image generator comprises:
a light module providing an input light beam;
an image scanner located in the optical path of said input light beam and adapted to split said input light beam into one or more light beam portions and directing said one or more of light beam portions to propagate with said projection angles $\alpha_{scn}$ relative to said general optical propagation path;
a light intensity modulator located in an optical path of at least one of said input light beam and said one or more light beam portions and adapted for controllably adjusting the intensity of one or more of light beam portions; and
a projection controller connectable to said light intensity modulator module and configured and operable to: obtain image data indicative of image pixels to be projected onto said retina and operate said light intensity modulator module for adjusting the intensities of said light beam portion in accordance with a value of a pixel of said image corresponding to said light beam portions respectively.

11. The eye projection system according to claim 10, wherein said projection controller is connectable to said image scanner and is operable to direct said light beam portion to propagate along with said projection angles $\alpha_{scn}$ relative to said general optical propagation path.

12. The eye projection system according to claim 10, wherein said light intensity modulator comprises a spatial light modulator configured and operable for splitting said input light beam into said plurality of light beam portions propagating along distinct respective optical paths, and said image scanner comprises a static optical module configured for deflecting said plurality of light beam portions towards different projection angles $\alpha_{scn}$.

13. The eye projection system according to claim 10, wherein said light intensity modulator is adapted to modulate the intensity of said input light beam and said image scanner comprises a scanning optical deflector configured and operable for splitting said input light beam in to said plurality of light beam portions, being temporal portions thereof and directing them to propagate towards different angles $\alpha_{scn}$ towards said eye projection optical module.

14. The eye projection system of claim 13, wherein said image scanning optical deflector and said gaze tracking deflector are actuated to control two or more degrees of freedom $\alpha_{in}$ and β of the propagation of said light beam portions such that each respective light beam portion for incident on the pupil with a desired pupil incidence angle $\alpha_{in}$ corresponding to the respective image pixel associated with the light beam portion relative to a gaze directions β associated to a line of sight of the eye.

15. The eye projection system of claim 14, wherein said gaze tracking adjustable optical deflector is configured and operable for controlling intersection locations of the light beam portions propagating towards the pupil with a substantially spherical portion of a virtual surface defining the possible locations of said pupil in different gaze directions; and said image scanning optical deflector is configured and operable for controlling an angle of intersection of said light beam portions with said substantially spherical portion of the virtual surface defining the possible locations of said pupil.

16. Eye glasses for projecting at least one of pure and augmented virtual reality comprising the eye projection system of claim 1.

17. The eye glasses of claim 16, configured for projecting augmented virtual reality to the eye, a lens of said eye glasses comprising a beam splitter/combiner surface adapted for reflecting light from the eye projection system towards the user eye and transmitting external light from a scenery towards the user's eye.

18. The eye glasses of claim 17, wherein the input light beam generated by a light module comprises one or more spectral bands, and said beam splitter/combiner surface is configured as a notch filter adapted for reflecting said one or more spectral bands towards the user's eye.

19. The eye glasses of claim 17, wherein the input light beam generated by the light module is polarized in a certain polarization, and said beam splitter/combiner surface is configured as a polarizer adapted for reflecting said certain polarization towards the user eye.

20. The eye projection system of claim 1 comprising:
a controller adapted to receive said data indicative of the image, which is to be projected onto a retina of the user's eye, and data indicative of said gaze direction β of said eye, and for projecting pixels of said image onto corresponding locations on said retina, wherein said projecting comprises carrying out the following for projection of each pixel of said image:
operating said light module to produce the light beam portion having intensity corresponding to an intensity value of said pixel in the image;
operating at least one of the image optical deflector and the gaze tracking deflector, by adjusting its deflection angle to direct said light beam portion in accordance with said gaze direction $\beta$ to be incident on a pupil of said user's eye; and
operating at least one of the image optical deflector and the gaze tracking deflector, by adjusting its deflection angle to direct said light beam portion to be incident on said pupil with a pupil incidence angle $\alpha_{in}$ corresponding to a location of said pixel in the image to thereby enable focusing, by an eye lens, said light beam portion associated with said pixel onto a location on the retina corresponding to said location of the pixel in the image.

21. An eye projection system comprising:
an image generator; and
an eye projection optical module, wherein:
said image generator is adapted to obtain data indicative of an image and produce a plurality of light beam portions corresponding to pixels of said image, adjust the intensity of each light beam portion of said light beam portions in accordance with a value of a pixel of said image corresponding to said light beam portion; and said image generator comprises an image optical deflector adapted to direct said light beam portion to propagate along a general optical propagation path towards said eye projection optical module with a projection angle $\alpha_{scn}$ relative to said general optical propagation path, where projection angle $\alpha_{scn}$ is determined in accordance with a location of said respective pixel in the image;
said eye projection optical module comprises a gaze tracking deflector configured and operable to be responsive to input signals indicative of a gaze direction $\beta$ of a user eye for deflecting the general optical propagation path of the light beam portions towards a pupil of said user eye in accordance with said gaze direction $\beta$; and wherein said general optical propagation path is deflected such that the light beam portions incident on the pupil with pupil incidence angles $\alpha_{in}$, corresponding to the projection angles $\alpha_{scn}$, with respect to a line of sight of said pupil associated with said gaze direction $\beta$, thereby directly projecting said image onto a retina of said eye at a substantially fixed location on the retina regardless of said gaze direction $\beta$ of the eye; and
wherein said image optical deflector and said gaze tracking deflector are adapted to control two or more degrees of freedom $\alpha_{in}$ and $\beta$ of the propagation of said light beam portions such that each respective light beam portion for incident on the pupil with a desired pupil incidence angle $\alpha_{in}$ corresponding to the respective image pixel associated with the light beam portion relative to a gaze directions $\beta$ associated a line of sight of the eye.

22. The eye projection system of claim 21, wherein said gaze tracking adjustable optical deflector is configured and operable for controlling intersection locations of the light beam portions propagating towards the pupil with a substantially spherical portion of a virtual surface defining the possible locations of said pupil in different gaze directions; and said image scanning optical deflector is configured and operable for controlling an angle of intersection of said light beam portions with said substantially spherical portion of the virtual surface defining the possible locations of said pupil.

* * * * *